United States Patent [19]
Ermer et al.

[11] Patent Number: 5,561,733
[45] Date of Patent: Oct. 1, 1996

[54] THERMALLY STABLE ELECTRO-OPTIC DEVICE AND METHOD

[75] Inventors: Susan P. Ermer, Redwood City; Doris S. Y. Leung, Palo Alto; Steven M. Lovejoy, San Francisco, all of Calif.

[73] Assignee: Lockhead Missiles & Space Company, Inc., Sunnyvale, Calif.

[21] Appl. No.: 436,073

[22] Filed: May 8, 1995

Related U.S. Application Data

[63] Continuation-in-part of Ser. No. 132,089, Oct. 5, 1993, Pat. No. 5,414,791.

[51] Int. Cl.$^6$ ........................................ G02B 6/00
[52] U.S. Cl. ........................................ 385/143; 560/35
[58] Field of Search ........................................ 385/141–145, 385/130; 560/35

[56] References Cited

U.S. PATENT DOCUMENTS

| | | | |
|---|---|---|---|
| 2,965,486 | 12/1960 | Brooker et al. | 430/58 |
| 4,145,215 | 3/1979 | Van Allan et al. | 430/58 |
| 4,264,694 | 4/1981 | Pu et al. | 430/58 |
| 5,093,883 | 3/1992 | Yoon et al. | 385/130 |
| 5,097,044 | 3/1992 | Phaff | 549/307 |
| 5,241,102 | 8/1993 | Syoshi et al. | 560/35 |

OTHER PUBLICATIONS

Ermer, S., et al., "DCM–Polyimide System for Triple–Stack Poled Polymer Electro–Optic Devices," in *Organic and Biological Optoelectronics* (Rentzepis, P.M., Ed.) Proc. SPIE 1853:183 (1993).

Ermer, S., et al., "Photobleachable Donor–Acceptor–Donor Chromophores with Enhanced Thermal Stability," in *Organic Thin Films for Photonic Applications Technical Digest* 1993, vol. 17 (Optical Society of America, Washington, D.C.) pp. 50–53 (1993).

Girton, D.G., et al., "20 GHz Electro–Optic Polymer Mach–Zehnder Modulator," *Appl. Phys. Lett.* 58(16):1730–1732 (1991).

Valley, J. F., et al., "Thermoplasticity and Parallel–Plate Poling of Electro–Optic Polyimide Host Thin Films," *Appl. Phys. Lett.* 60(2):160–162 (1992).

Van Eck, T. E., et al., "Complementary Optical Tap Fabricated in an Electro–Optic Polymer Waveguide," *Appl. Phys. Lett.* 58(15):1588–1590 (1991).

Wu, J. W., et al., "Thermal Stability of Electro–Optic Response in Poled Polyimide Systems," *Appl. Phys. Lett.* 58(3):225–227 (1991).

*Primary Examiner*—Akm E. Ullah
*Attorney, Agent, or Firm*—Vincent M. Powers; Peter J. Dehlinger

[57] ABSTRACT

Novel acceptor-donor-acceptor and donor-acceptor-donor compound for use in forming a thermally-stable electro-optic waveguide are disclosed. Also disclosed is a thermally stable waveguide material containing thermally stable acceptor-donor-acceptor or donor-acceptor-donor guest dipole compounds in a temperature-resistant polymer matrix. The waveguide has selected regions in which the net dipoles of the guest molecules are oriented, for electro-optic switching when an electric field is placed across these regions.

29 Claims, 11 Drawing Sheets

(III)

(IV)

Photobleaching

Poling

Cladding, Electrode layer

Poling

THERMALLY STABLE ELECTRO-OPTIC DEVICE AND METHOD

This application is a continuation-in-part of Ser. No. 08/132,089 filed Oct. 5, 1993, U.S. Pat. No. 5,414,791, which is incorporated herein by reference.

FIELD OF THE INVENTION

The present invention relates to electro-optic devices and to thermally stable compounds and materials used in forming such devices.

REFERENCES

Boyd, R. H., in *Methods of Experimental physics*, Vol. 16c, R. A. Fava, Editor, Academic Press, New York (1980), pp. 379–421.

Ermer, S., et al., Appl Phys Lett 61(19):227–274 (1992).

Girton, D. G., et al., Appl Phys Lett, 16(22):17–30 (1991).

McCrum, N. G., et al., *Anelastic and Dielectric Effects in Polymeric Solids*, Wiley, New York, 1967.

Takahashi, D. Y., et al., Macromolecules, 17:2583 (1984).

Van Eck, T. E., et al., Appl Phys Lett, 58 (15): 1588 (1991).

Wu, J. W., et al., Appl Phys Lett, 58(3): 225 (1991).

BACKGROUND OF THE INVENTION

Poled electro-optic (EO) polymers are a new class of materials which, in waveguide applications, have demonstrated the promise of high bandwidth, lower power dissipation, and ease of integrated fabrication with existing electronics (i.e., silicon). One of the major obstacles to be overcome with such polymers is the decay of the EO response at the elevated manufacturing and operating temperatures dictated by current electronics technology.

Decay of the EO response at elevated temperatures in poled polymers is due to the relaxation of the dipole alignment induced during poling by a dc electric field. Recent efforts to achieve poled EO thermal stability include making long side-chain polymers with high glass transition temperatures and providing epoxy cross-linking during poling.

For generally useful devices, higher temperature EO thermal stability is required. For example, typical manufacturing process short-term temperature excursions can be higher than 300° C. To meet fabrication requirements alone, the poling and curing temperature of an EO polymer for integrated devices should exceed this mark.

SUMMARY OF THE INVENTION

The invention includes, in one aspect, a compound of the form:

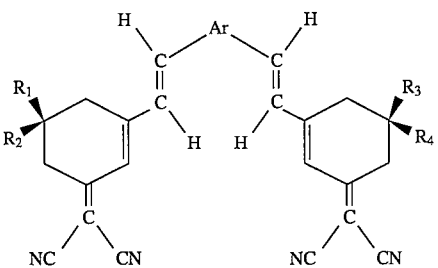

where Ar is an aromatic fused ring structure having a ring-contained tertiary amine, and $R_1$, $R_2$, $R_3$, and $R_4$ are the same or different and are each selected from the group consisting of each H, an alkyl group or a substituted alkyl group.

In one preferred embodiment, Ar is a carbazole group, such as shown in the structure below:

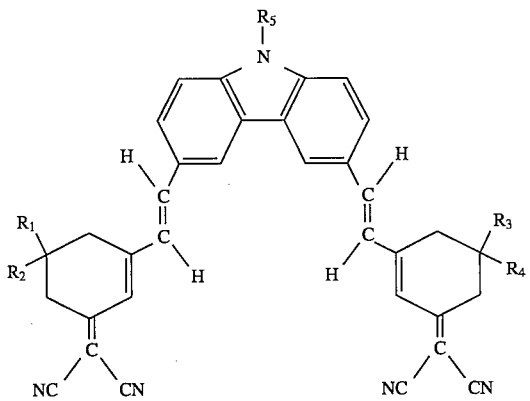

where $R_1$–$R_4$ are as above, and $R_5$ is a lower alkyl, substituted lower alkyl, cycloalkyl, substituted cycloalkyl, alkenyl, alkynyl, aryl, or alkaryl group.

In another aspect, the invention includes an electro-optic waveguide material. In one general embodiment, the material comprises a heat-stable polymer matrix having dissolved therein, thermally stable guest dipolar molecules, such as the acceptor-donor-acceptor molecule above, or a donor-acceptor-donor molecule of the general form:

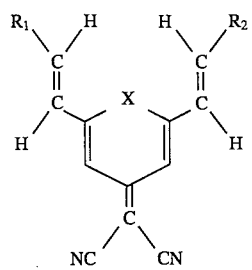

wherein X is O, S, $CH_2$, or NR, where R is a lower alkyl group; and $R_1$ and $R_2$ are either fused ring structures having a ring-contained tertiary amine or are 2-(dialkylamino)thienyl rings. The compound in accordance with the above structure preferably takes the form of one of the structures shown at A1–A3 below:

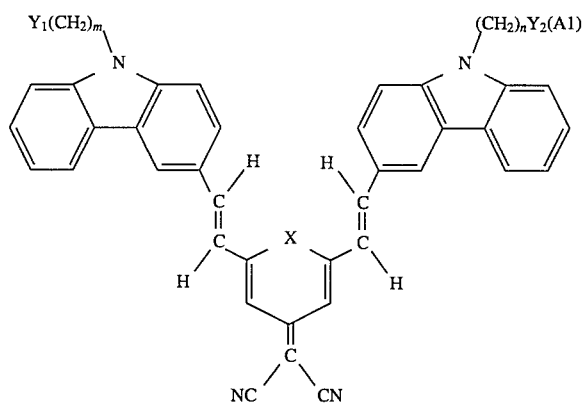
(A1)

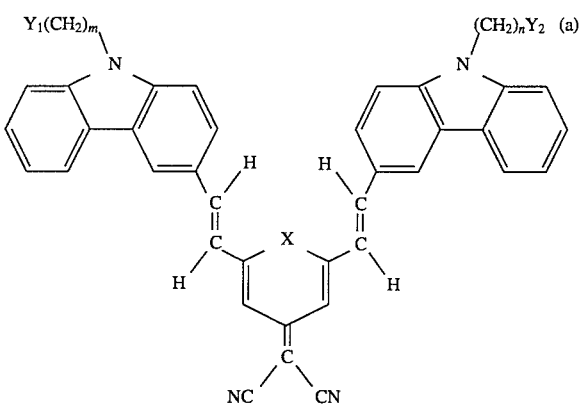
(a)

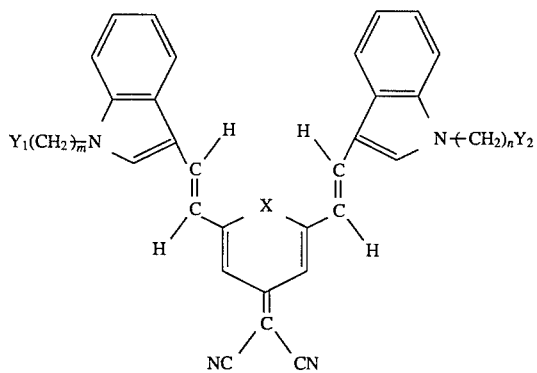
(A2)

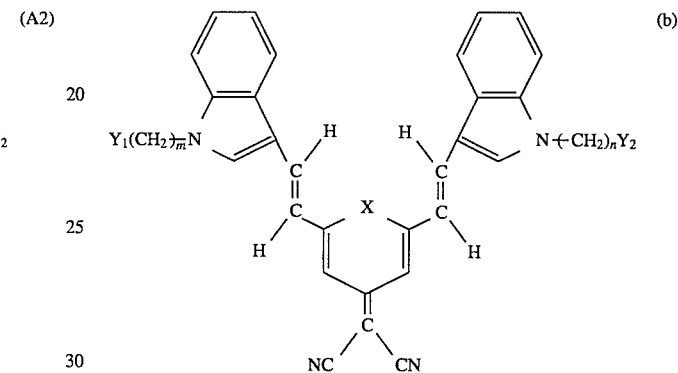
(b)

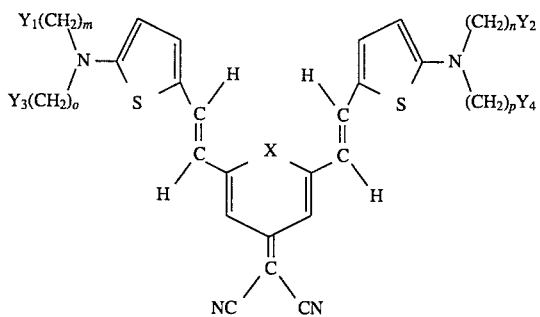
(A3)

wherein X is O, S, CH$_2$, or NR, where R is a lower alkyl group; Y$_1$, Y$_2$, Y$_3$ and Y$_4$ are separately H or OH; and m, n, o and p are separately integers from 2 to 7; or Y$_1$ and Y$_3$ taken together are —CH$_2$CH$_2$—, forming a cyclic amine wherein the sum of m+o is an integer from 0 to 2, and Y$_2$ and Y$_4$ taken together are —CH$_2$CH$_2$—, forming a cyclic amine wherein the sum of n+p is an integer from 0 to 2.

In another embodiment, the waveguide material comprises guest dipole subunits having a structure selected from the group consisting of:

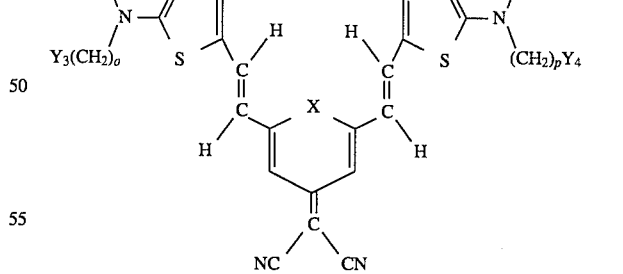
(c)

(d)

wherein X is O, S, $CH_2$, or NR, where R is a lower alkyl group; $Y_1$, $Y_2$, $Y_3$ and $Y_4$ are separately H, OH, or OL where L is a polymer linker subunit, and at least one of $Y_1$ and $Y_2$ is OL; and m, n, o and p are separately integers from 2 to 7. The guest dipole molecules (subunits) are covalently attached to polymer linker subunits to form a heat-stable polymer matrix.

The guest molecules (and guest subunits) have net dipole moments, and these dipole moments are oriented or poled in waveguide-channel regions of the material, such that the index of refraction in the channel regions can be modulated for optical switching purposes by applying an electric field across the regions.

In one general embodiment, the dipolar molecules in non-channel regions of the material have been photobleached. In this embodiment, the regions of oriented dipolar molecules may include the entire waveguide channel or only switching regions thereof.

In another general embodiment, the dipolar molecules are oriented in the waveguide channel, and randomly oriented in non-channel regions.

Also forming part of the invention is an electro-optic device having a substrate, and formed on the substrate, an electro-optic waveguide channel formed of a waveguide material of the type discussed above. The waveguide has switching regions in which the net dipole moments of the guest dipole molecules are oriented such that the index of refraction of the switching regions can be modulated for optical switching purposes by applying an electric field across the regions. Electrodes positioned adjacent the switching regions are used in creating the switching fields. In one preferred embodiment, the polymer matrix used is a polyimide matrix.

In still another aspect, the invention includes a method of forming an electro-optic waveguide having EO switching regions. The method includes forming a layer of a polymer material composed of an uncured polymer matrix having dissolved therein, randomly oriented guest dipole molecules of the type described above. The layer is heated to a temperature above the glass-melting temperature, $T_g$, and at least 250°–350° C., allowing movement of the dipolar molecules in the polymer matrix. During the heating step, an electric field is applied across the layer, or selected regions thereof, corresponding to the waveguide channel or switching regions in the channel, causing the dipolar molecules to orient with their net dipole moments aligned with the electric field.

The heating step may be used to allow reorienting of the dipole molecules, or may additionally be used as a final curing step.

The invention also includes a novel donor-acceptor-donor compound having a structure selected from the group consisting of structures (a'), (b'), (c') and (d') (which correspond to the above structures (a), (b), (c) and (d), respectively), wherein X is O, S, $CH_2$, or NR, where R is a lower alkyl group; $Y_1$, $Y_2$, $Y_3$ and $Y_4$ are separately H or OH, where at least one of $Y_1$ and $Y_2$ is OH; and m, n, o and p are separately integers from 2 to 7. In two preferred embodiments, X is O or S. The compounds are useful in forming waveguide materials of the type discussed above, and in particular, in forming a polymer matrix to which the guest dipole molecules are covalently bound.

These and other objects and features of the present invention will become more fully apparent when the following detailed description of the invention is read in conjunction with the accompanying drawings.

DETAILED DESCRIPTION OF THE DRAWINGS

I. Definitions

Figure 1A:
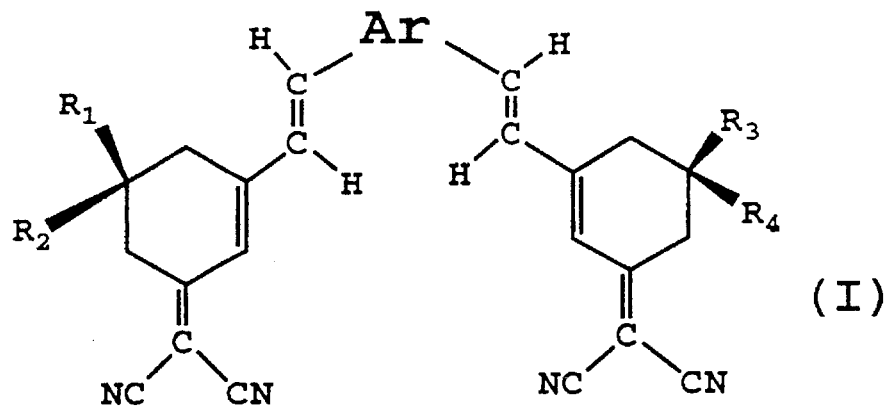
FIGS. 1A–1D show the molecular structures of a general type acceptor-donor-acceptor (ADA) dipolar photoabsorbing compound in accordance with the invention (FIG. 1A); exemplary aryl groups which can serve as the "Ar" group in the FIG. 1A compound (FIG. 1B); and two resonance structures of a preferred embodiment of the compound (FIGS. 1C and 1D)

As used herein, the terms below have the following meaning, unless indicated otherwise:

"Aromatic fused ring structure" refers to a fused 5-, 6-, or 7-member carbon atom or heteroatom ring system having an aromatic π electron system. Exemplary fused ring structure included a carbazole moiety, which has a 6-5-6 fused ring structure, and an indole moiety, which has a 6-5 fused ring structure. Additional examples of fused ring structures are shown in FIG. 1B.

A "fused ring structure having a ring-contained tertiary amine" means that the fused ring structure contains a nitrogen atom having two ring-atom bonds, and a third bond to a non-hydrogen radical, such as an alkyl group. An exemplary compound of this type is an N-ethylcarbazole group.

An "alkyl group" refers to an alkyl or substituted alkyl group having 1 to 20 carbon atoms, such as methyl, ethyl, propyl, and the like. Similarly, "cycloalkyl group" refers to a saturated carbocyclic ring group which may have alkyl, aryl, aralkyl substituents such as cyclopropyl, cyclopentyl, cyclohexyl, and the like, or a substituted form thereof. By "substituted" is generally meant that the group is derivatized with one or more small chemical moieties, such as methoxy, ethoxy, halogen, hydroxy, and ethylene oxide, for example.

"Lower alkyl" as used herein refers to straight chain and/or branched chain alkyl groups containing from 1 to 6 carbon atoms, e.g., methyl, ethyl, propyl, isopropyl, tert-butyl, isobutyl, n-hexyl, and the like.

An "alkenyl group" refers to a hydrocarbon group containing a carbon-carbon double bond, such as vinyl, allyl, cyclopentenyl, and the like.

An "aryl group" refers to an aromatic ring group having 5–20 carbon atoms, such as phenyl, naphthyl, anthryl, or to alkyl or aryl substituted aryl groups such as tolyl, ethylphenyl, biphenylyl, etc. Also included are heterocyclic aromatic ring groups having one or more nitrogen, oxygen, or sulfur atoms in the ring.

An "alkaryl group" refers to an aryl-substituted alkyl group such as benzyl, phenethyl, etc.

"Alkoxy" refers to alkyloxy groups where alkyl is as defined above, such as methoxy, ethoxy, isopropoxy, butoxy, etc. "Aryloxy" refers to groups where aryl is as defined above, such as phenoxy, naphthoxy, etc.

"Dipolar molecules" are molecules having a net dipole moment, and thus capable of being oriented in an electric field.

A "polymer matrix" refers to the bulk polymer phase in a glassy polymer material containing dipolar molecules of the type discussed herein. The matrix is fluidic before hardening, rigid after hardening or curing, and sufficiently fluidic with heating at the glass-transition temperature to allow dipolar molecules in the matrix to orient in response to an electric field applied across the matrix. The guest dipole molecules may be dissolved in a polymer matrix or may be covalently attached subunits within a polymer, as discussed below.

A "heat-stable polymer matrix" refers to a polymer matrix which is resistant to decomposition at the temperatures necessary to pole guest dipole molecules within the matrix, as well as the high temperatures typical in the manufacture of waveguides and integrated circuits.

A dipolar molecule is "dissolved" in a polymer matrix if it is present in the matrix in solute or free form, that is, in an unaggregated state.

"Glass-transition temperature" refers to the temperature in thermostable polymer at which a hardened polymer shows a transition toward more mobile polymer chains, as evidence by dielectric spectroscopy.

A "waveguide" is an optical structure capable of guiding a beam of laser light along light channels in the waveguide. The waveguide includes both the light channel(s) in which light waves propagate in the waveguide, and surrounding cladding which confine the waves in the channel.

II. Synthesis of Dipolar Molecules

In accordance with one aspect of the invention, there are provided thermally stable guest dipole compounds which are useful for electro-optical applications. The compounds show high temperature stability and high sublimation temperatures, making them compatible with heating procedures employed in device manufacture. Thus, not only are the guest dipole compounds of the invention able to withstand short-duration, high temperature excursions that typically occur during semiconductor processing, but also they permit the curing of polymer matrices for the recommended time and temperature without damaging the guest molecules, resulting in a more fully densified system with a higher $T_g$.

For wave-guide use in particular, further advantages include low light absorbance at device wavelengths, photobleachability, compatibility with polyimide-type host materials, and availability from commercial sources or standard synthetic techniques.

As detailed below, the compounds of the invention contain either one donor moiety and two acceptor moieties, or two donor moieties and one acceptor moiety. The donor moieties generally contain a ring-contained tertiary amine nitrogen atom, or a ring-attached tertiary amine (as in 4-(dialkylamino)phenyl), as a donor group capable of donating electrons to the adjacent aromatic ring structure. Likewise, each acceptor moiety contains a gem dinitrile as an acceptor group, capable of accepting electrons. The donor and acceptor groups are linked via a conjugated bonding system comprised of alternating single and double bonds, enabling the formation of a charge dipole by resonance delocalization.

Figure 1B:
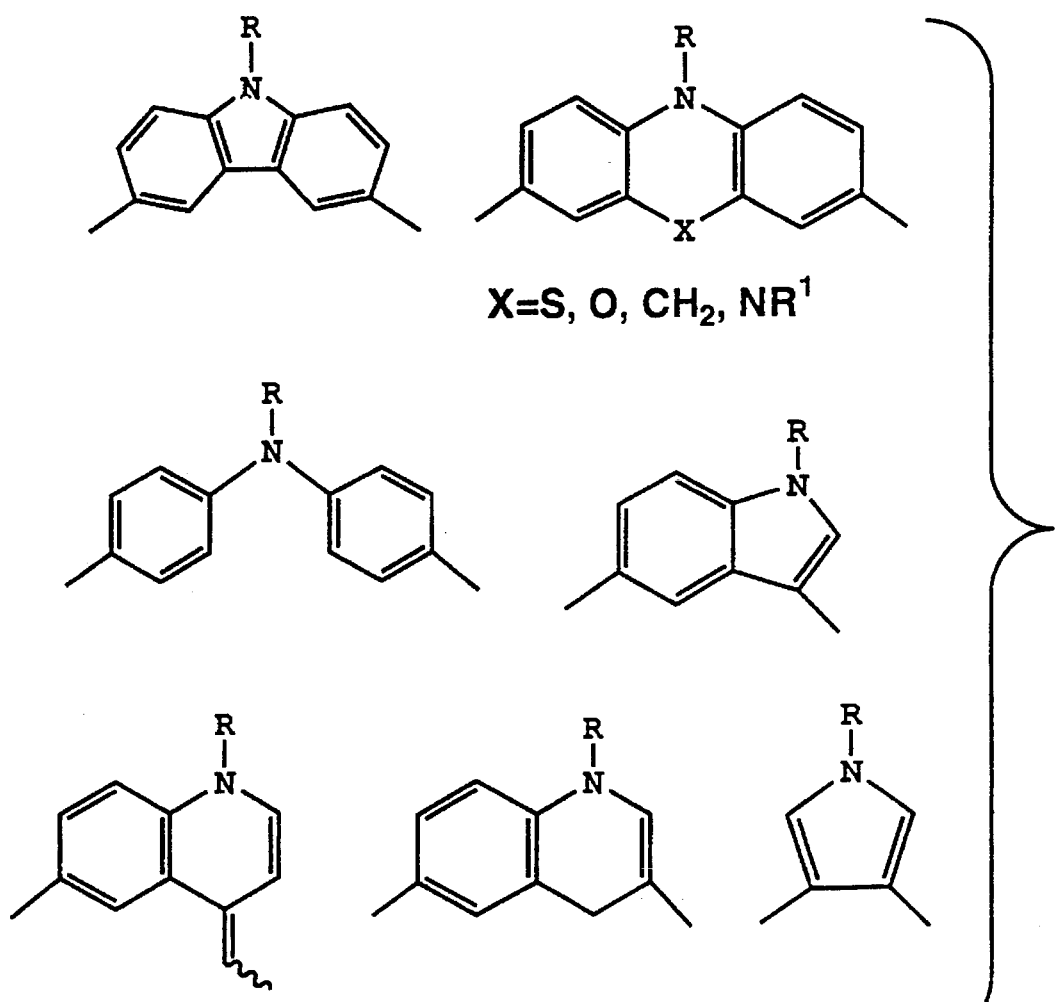

FIG. 1A shows the molecular structure of a general electron acceptor-donor-acceptor (ADA) dipolar compound of the invention (Compound I). The donor moiety (Ar) is an aromatic fused ring structure having a ring-contained tertiary amine (donor group). Attached to the donor moiety at two different ring-atoms are two acceptor groups which each contain a gem dinitrile group as electron acceptor. The donor group is conjugated to each acceptor group via a series of alternating single and double bonds.

Exemplary aryl groups which can be used as "Ar" are shown in FIG. 1B, where for $X=NR^1$, $R^1$ is a lower alkyl or substituted lower alkyl group; and $R_5$ is a lower alkyl, substituted lower alkyl, cycloalkyl, substituted cycloalkyl, alkenyl, alkynyl, aryl, or alkaryl group. Of the structures shown in FIG. 1B, the top five structures are examples of fused ring structures having a ring-contained tertiary amine. The structure at the lower left of FIG. 1B illustrates another embodiment, wherein the "Ar" group includes a tertiary nitrogen atom which is linked to two acceptor moieties via benzene rings. The structure at the lower right of FIG. 1B illustrates an embodiment where the "Ar" group is an imidazole ring that contains a tertiary nitrogen atom and which is linked to two acceptor moieties via the 3- and 4-positions of the pyrrole ring.

In FIG. 1B, the exemplary "Ar" groups are shown as being attached to the acceptor moieties at ring positions on the "underside" of each donor ring system, opposite the side (the "upper side") where the donor nitrogen atom is located. For example, where "Ar" is a carbazole (upper left of FIG. 1B), the donor nitrogen is located on the "upper side" of the ring system, and the linkages for the acceptor moieties are located at carbazole ring positions 3 and 6 (lower side of ring system). However, the invention also contemplates acceptor-donor-acceptor compounds of the general type shown in FIGS. 1A and 1B, where the acceptor groups are attached at other ring positions on the donor moiety besides those shown, such that a dipolar compound is formed. For example, with respect to the two "Ar" groups shown in the top row of FIG. 1B, the acceptor moieties may be linked to the 1 and 8 carbon atoms of the carbazole ring (upper left of FIG. 1B), or to the carbon atoms ortho to the tertiary nitrogen in the "Ar" group shown at the upper right of FIG. 1B. In such compounds, the acceptor groups are located on the same side of the ring system as the tertiary amine (electron donor), but the acceptor and donor groups are spaced sufficiently far apart to provide good dipolar character.

Figure 1C:
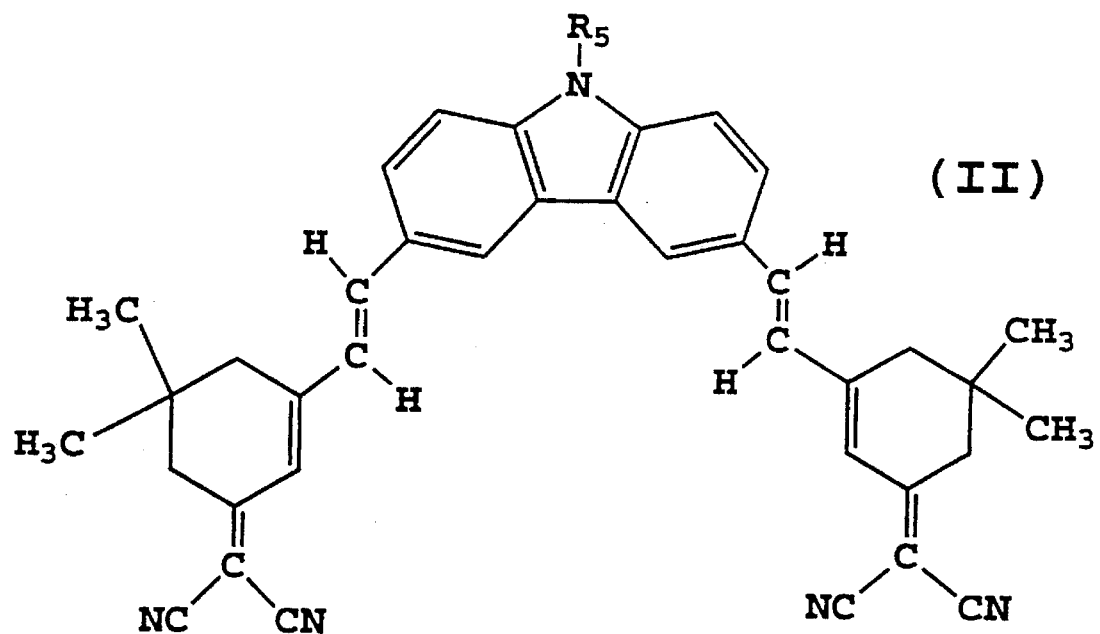

The structure of a preferred embodiment of the ADA compound from FIG. 1A is shown in FIG. 1C, where the donor is an N-substituted carbazole group; that is, the carbazole group contains a tertiary amino group within the fused ring, where the radical group $R_5$ is a lower alkyl or substituted lower alkyl group. Preferred R groups include methyl, ethyl, propyl, 2-hydroxyethyl, and 3-hydroxypropyl.

The acceptor moieties in the FIG. 1C compound are 3-vinyl-1-dicyanomethylidene cyclohexene rings which may be substituted at the 5-ring-carbon position with one or more groups selected from the group consisting of hydrogen, a lower alkyl group, or substituted lower alkyl groups ($R_1$, $R_2$, $R_3$ and $R_4$).

Figure 1D:
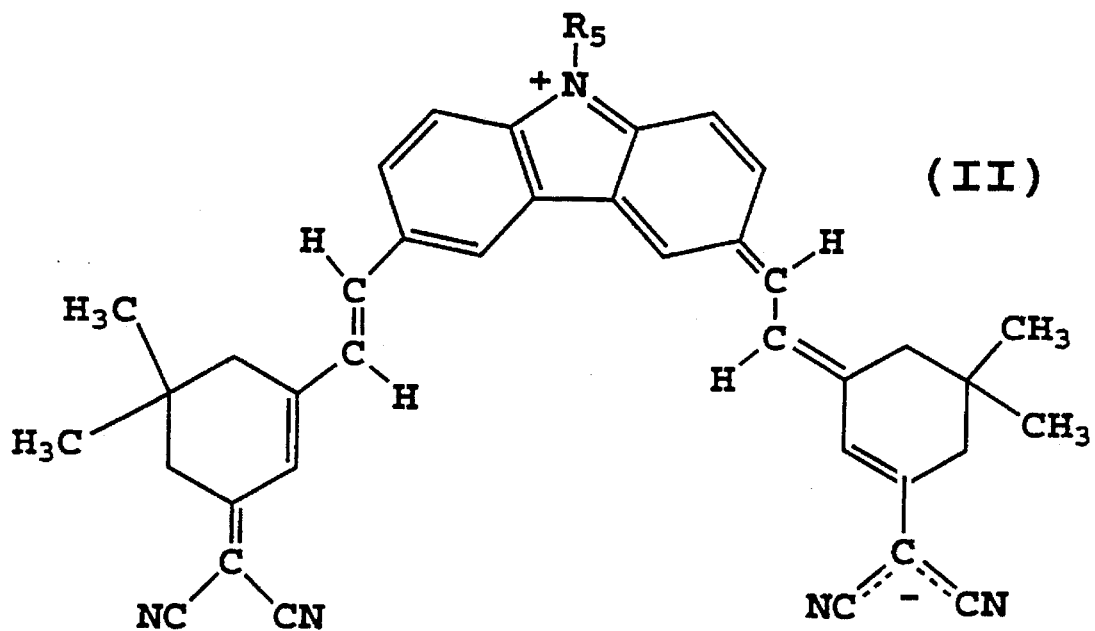

It can be seen from FIG. 1C that the gem dinitrile group (=C(CN)$_2$) in each acceptor moiety is located at the end of a conjugated bonding system which terminates at its other end with the tertiary amino group in the donor moiety, thus allowing formation of a resonance structure of the type shown in FIG. 1D.

Figure 2A:
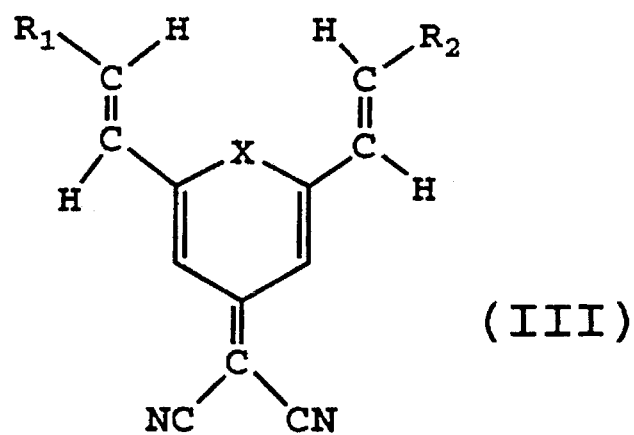
FIGS. 2A and 2B show molecular structures of a general donor-acceptor-donor (DAD) type dipolar photoabsorbing compound employed in an electro-optical material formed in accordance with the invention (FIG. 2A) and a preferred embodiment of the compound (FIG. 2B)

FIG. 2A shows the molecular structure of a general donor-acceptor-donor (DAD) dipolar compound in accordance with one embodiment of the invention. Here, the acceptor moiety includes a 2,5-unsaturated 6-member cycloalkane or heterocyclic ring having a dicyanomethylidene (gem dinitrile) group attached to the 4 position, and where X is O, S, CH$_2$, or NR, and R is a lower alkyl or substituted lower alkyl group. The acceptor moiety is linked via its 2- and 6-ring position vinyl groups to donor moieties $R_1$ and $R_2$, which are fused ring structures having a ring-contained tertiary amine, as defined above, with the exception that in the DAD-type compounds in FIG. 2A, each fused ring structure ($R_1$ and $R_2$) is linked to only one acceptor moiety.

Figure 2B:
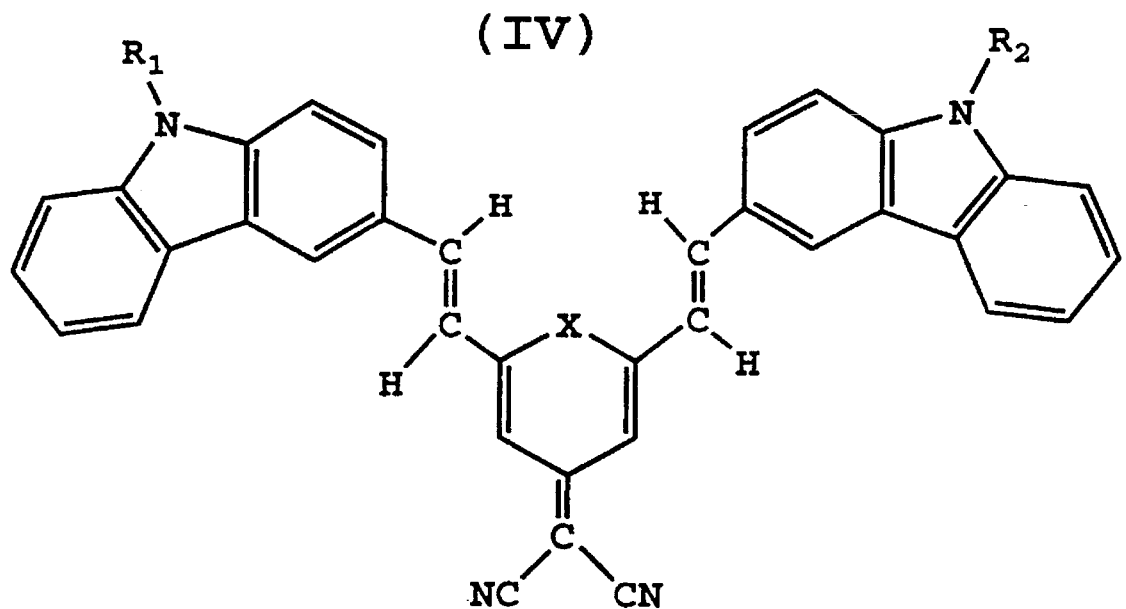

FIG. 2B shows the molecular structure of a preferred embodiment of the FIG. 2A compound, wherein the donor moieties $R_1$ and $R_2$ (FIG. 2A) are N-substituted carbazole groups, and X is O. As with the compounds in FIG. 1C, the carbazole structure includes a tertiary amino group as an electron-donor group. The $R_3$ and $R_4$ groups may be the same or different and are as defined for $R_5$ in the DAD-type compounds above. As with the FIG. 1A compounds, the donor groups are conjugated to an acceptor group via alternating single and double bonds.

Figure 3:
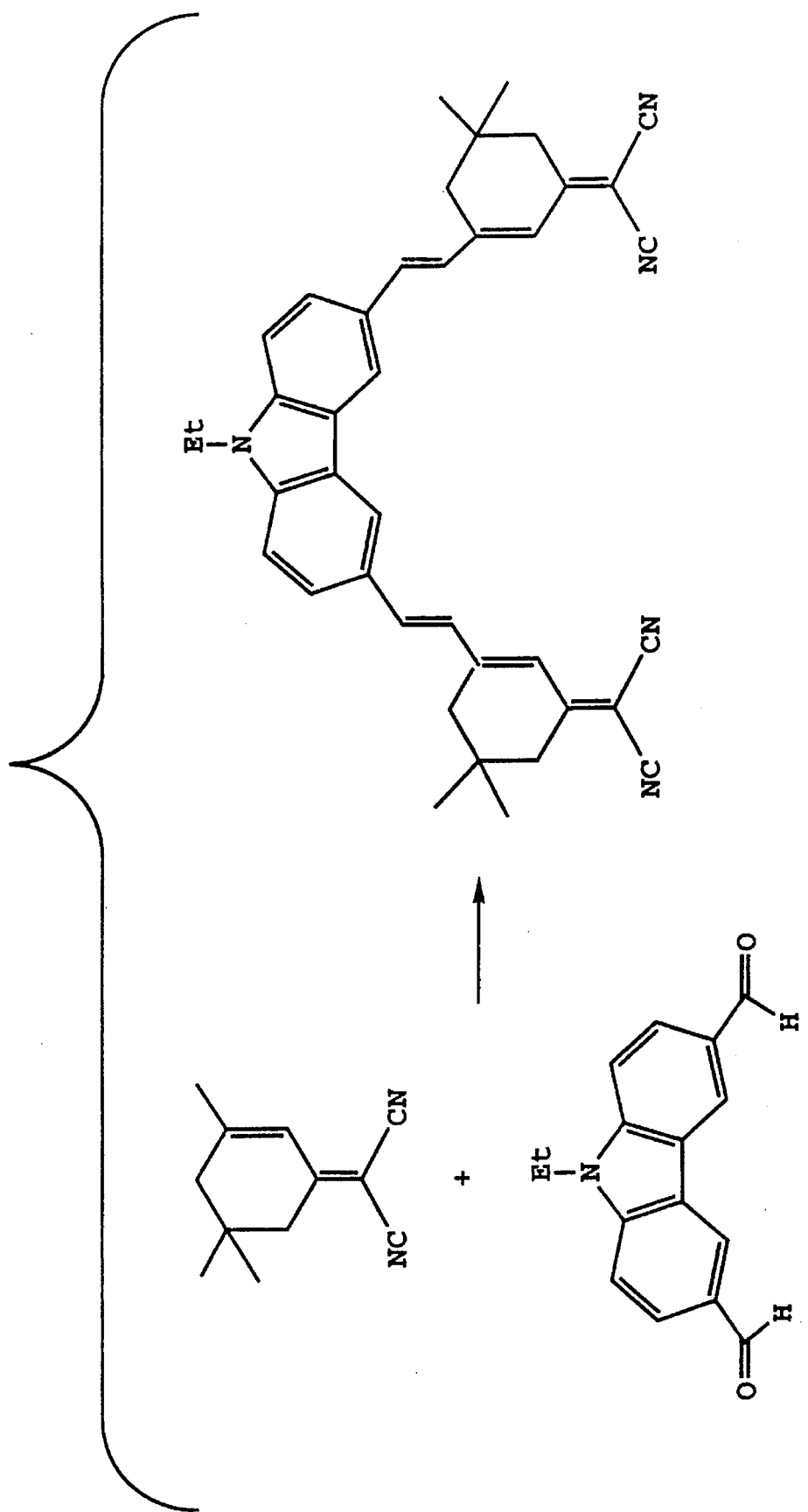
FIG. 3 illustrates a synthesis of the dipolar photoabsorbing compound shown in FIG. 1C.
Figure 4:
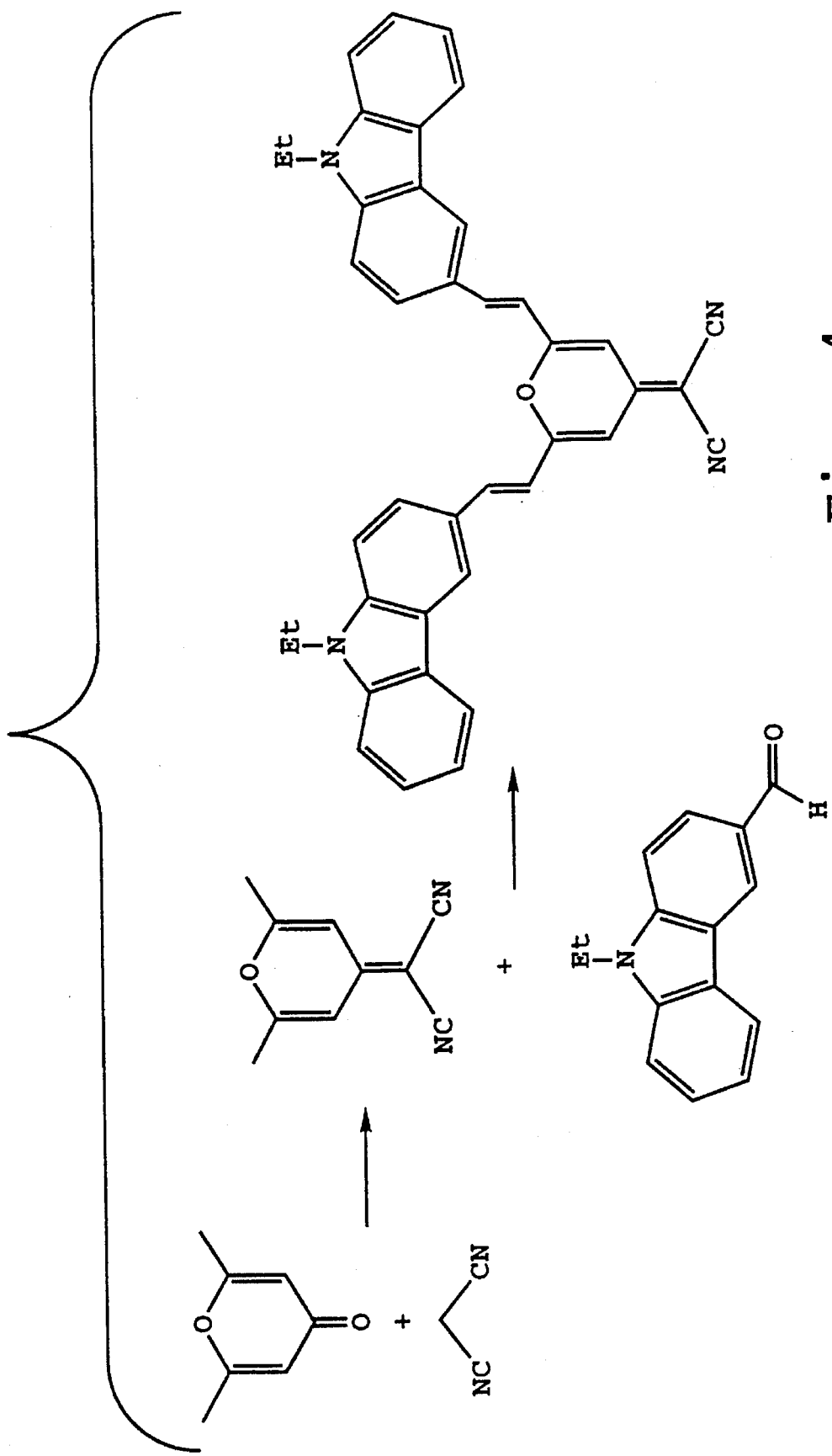
FIG. 4 illustrates a synthesis of the dipolar photoabsorbing compound shown in FIG. 2B.

FIGS. 3 and 4 illustrate synthetic schemes for preparing the guest molecules shown in FIGS. 1C and 2B, respectively. In FIG. 3, the ADA compound is prepared by first forming dinitrile V in situ, by reaction of isophorone with 1 equivalent of malononitrile in the presence of acetic anhydride, acetic acid, and piperidine. The mixture is stirred at room temperature for an hour, and then at 80° C. for an additional hour. 9-Ethyl-9H-carbazole-3,6-dicarboxaldehyde (VI) is then added, and the mixture is stirred overnight at 80° C. The desired product VII is then isolated by passage through silica gel, followed by recrystallization as detailed in Example 1.

More generally, compounds in accordance with the FIG. 1A structure can be prepared by reaction procedures analogous to that shown in FIG. 3. Specifically, dinitrile V is reacted with the appropriate dialdehyde form of the aromatic fused ring moiety, resulting in the coupling of each aldehyde carbon atom to the 3-methyl carbon from a dinitrile compound. The resultant linkages place the donor nitrogen atom in conjugation with the nitrile groups in each acceptor moiety.

With reference to FIG. 4, DAD-type compound X can be prepared by reacting (2,6-dimethyl-4H-pyran-4-ylidene)propanedinitrile (VIII) with 2 equivalents of 9-ethyl-9H-carbazole-3-carboxaldehyde (IX) in the presence of base (piperidine). The desired product (X) can be isolated by recrystallization, as detailed in Example 2.

More generally, compounds in accordance with the structure shown in FIG. 2A can be prepared by suitable modification of the scheme shown in FIG. 4. Specifically, dinitrile VIII is reacted with the appropriate dialdehyde form of the aromatic ring moiety being added as electron donor, resulting in the coupling of each aldehyde carbon atom to the 2- and 6-methyl carbons of VIII. The resultant linkages place the electron donor nitrogen atom in electronic conjugation with the two nitrile groups in each acceptor moiety. Several illustrative syntheses are given in Examples 2–5.

In one general embodiment, the dipolar compounds of the invention include a ring-contained tertiary amine as electron donor; i.e., where the amine nitrogen has three substituents, two of which are part of the same ring (e.g., see the top five structures in FIG. 1B). It is hypothesized that the presence of the tertiary amine nitrogen within the ring enhances the thermal stability of the dipolar compound.

Alternatively, with regard to the DAD-type compounds, the donor groups may be non-fused rings such as 4-(dialkylamino)phenyl (Example 4) or 2-(dialkylamino)thienyl (Example 5).

It will be appreciated that the dipolar compounds of the types shown in FIGS. 1A and 2A can be modified to contain additional substituents to alter the solubility and physical properties of the compounds. Such substituents can be added to the ring structures of the donor and/or acceptor moieties after, or preferably, prior to coupling to form the dipolar compound. Alternatively, such substituents can reside on one or more of the tertiary nitrogens associated with the electron donor groups. By increasing the molecular weight of the compound, the added substituents can further inhibit volatilization of the compound at elevated temperatures, particularly with dipolar compounds having smaller fused-ring structures. In addition, such substituents can be used to add groups which enhance the solubility of the compound in, for example, the types of solvents in which polyimide precursors are soluble. Exemplary groups for improving solubility properties include hydroxyl-substituted alkyl groups, such as hydroxyethyl, and 2- or 3-hydroxypropyl, for example.

In experiments conducted in support of the invention, the applicants have found that DAD compounds of the type shown at structures (a) through (d), but wherein the amino groups are derivatized with methyl groups exhibit poor solubility in chloroform, and thus, poor solubilities in the polymer matrices of the invention. Accordingly, the amino groups of the DAD compounds in structures (a) through (d) and (a') through (d') above have alkyl substituents that are no shorter than ethyl, to obtain good solubility properties.

It will also be appreciated that the compounds of the invention can be modified to include substituents compatible with covalent linkage to a polymer matrix. Such substituents include alkenyl such as vinyl and allyl groups, acrylate groups, acrylamide groups, and the like; alkynyl groups; epoxide groups; and hydroxylated alkyl groups for example. The substituent(s) may be added to one or more of the various ring positions in the dipolar compound (or a precursor of the dipolar compound), including the donor nitrogen atom. The particular substituent is selected according to the chemical properties of the polymer to which the dipolar compound is being attached. With the Cyclotene™-type polymers (Dow), for example, the substituent preferably contains a carbon-carbon double bond, for reacting by cycloaddition (Diels-Alder) with the Cyclotene subunits to form covalent linkages to the polymer matrix.

In one preferred embodiment, guest dipole molecules of the invention are incorporated into a polymer matrix using dipole molecules (quest dipole subunit precursors) derivatized with hydroxyl-containing alkyl groups, such as donoracceptor-donor compounds in accordance with structures (a), (b), (c) and (d) above. These compounds are characterized by the presence of carbazole, indole, 4-dialkylaminophenyl, and 2-dialkylaminothienyl groups as electron donors, and a gem dinitrile as electron acceptor. The donor groups include hydroxyl substituents which are useful for covalent incorporation into a polymer matrix. These compounds may be readily synthesized by the methods discussed above, and by suitable adaptation of the syntheses described in Examples 2 through 5.

In a preferred embodiment, hydroxylated guest dipole compounds in accordance with structures (a), (b), (c), and (d) above are covalently incorporated into a polymer chain or polymer matrix by reaction with suitable linker subunit precursors to form copolymers having advantageous electrooptic and heat-stable properties. Such copolymers are useful for forming waveguide materials as discussed below.

With continued reference to structures (a)–(d) and (a')–(d') above, the parameters m, n, o, and p may be the same or different, but are preferably the same for the sake of synthetic convenience. The number of hydroxyl groups in the compounds may likewise vary, depending on the number of hydroxyl groups needed for optimal covalent incorporation into the waveguide polymer, as discussed below.

The polymer linker subunits are selected to be reactive with hydroxyl groups in the guest dipole molecules. The polymer linker subunit may itself consist of one or more monomers. Suitable linker subunit precursors include: substituted polystyrenes, polyquinolines, epoxides, linear polyalkyleneoxides, such as polyethylene oxide (polyethyleneglycol, PEG), polyacrylamide, polymethacrylamide, polyvinylalcohol, polyvinylpyrrolidone, polyvinyloxazolidone, polyimides, polycarbonates, polyacrylates, polyarylethers, polyesters, and polyurethanes, including copolymers thereof. Preferably, the linker subunits are provided by a polyquinoline or substituted polystyrene monomer.

The copolymer that is formed of dipole subunits and linker subunits may take the form of linear and/or branched chains, or may consist of a crosslinked three-dimensional matrix. Thus, where the dipole subunits contain two, three or four hydroxyl groups, the subunits allow crosslink formation with two or more linker subunits in the copolymer matrix. Alternatively, the dipole subunits are incorporated into an alternating copolymer chain in which the dipole subunits are spaced apart by intervening linker subunits. For these embodiments, the dipole subunit precursor contains at least two hydroxyl substituents which are situated on the same donor group (e.g., $Y_1$ and $Y_2$ in structure (d') above), or alternatively, are situated on separate donor groups in the DAD structure (e.g., $Y_1$ and $Y_3$). Thus, the invention contemplates an embodiment wherein $Y_1$ and $Y_2$ of the precursor DAD compounds are both OH, and $Y_3$ and $Y_4$ (structures (c), (c'), (d) and (d')) are H; and an alternate embodiment wherein $Y_1$ and $Y_3$ are OH and $Y_2$ and $Y_4$ are H (structures (c), (c'), (d) and (d')).

In yet another embodiment, the copolymer takes the form of a linear linker subunit backbone with pendant guest dipole molecules attached to suitable attachment sites along the backbone. For this embodiment, the guest dipole molecule need only contain one hydroxyl group for covalent linkage, although additional hydroxyls (which may or may not react with other backbone attachment sites) may also be present. Thus, the invention contemplates quest dipole subunit precursors that contain one, two, three, or four hydroxyl "$Y_n$" groups with the remainder being H.

Covalent attachment of the guest dipole subunits to the linker subunits may be accomplished by any of a number of standard methods in polymer chemistry. For example, the linker subunits may be situated in a preformed polymer of linker subunits, such as polyacrylate or hydroxyl-substituted polystyrene, which can then be reacted with the selected hydroxylated guest dipole subunit precursor to form the desired copolymer product. Alternatively, in a more preferred embodiment, polymer formation is carried out in two steps, by first covalently joining linker subunit precursor monomers with the selected DAD compound, and then polymerizing the DAD-linker subunit monomers to form the desired product.

The guest dipole subunits are covalently linked to the linker subunits by standard polymerization techniques as described, for example, in "Polymer Synthesis", Volumes 1 and 2, 2nd edition, edited by S. R. Sandler and W. Karo, Academic Press, 1992; see also McCulloch, I. A., *Macromolecules* 27:1697 (1994).

Where the linker precursor contains free carboxylic acid groups, the precursor may be covalently linked with hydroxyl groups in the guest molecule to form a copolymer product containing ester linkages. Such reactions are accomplished by methods known in the art. Typically, the reaction is carried out in the presence of solvent and a catalytic amount of acid or base, followed by isolation of the desired polymer product. Oxygen-carbonyl linkages are formed where the polymer linker precursor is a polycarbonate, polyacrylate, or polyurethane, for example. The guest dipole subunits and polymer linker subunits may also be joined by ether linkages, by condensation of hydroxyl group(s) of the guest dipole molecules with a hydroxyl group in the linker subunit precursors. For incorporation into a polyimide-type polymer, exemplary methods can be found in Becker, M. W. et al., *Chem. Mater.* 6:104 (1994) and Yu, D. et al. *Appl. Phys. Lett.* 66:1050 (1995).

III. Physical Properties

Figure 9:
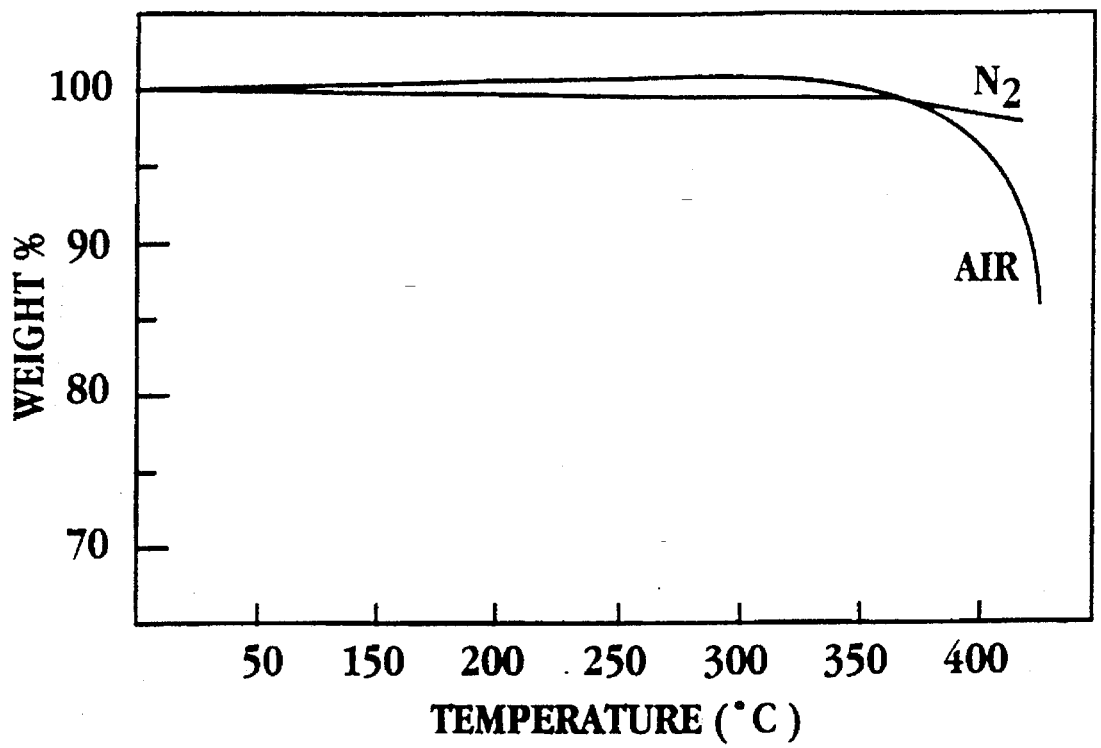
FIG. 9 shows a thermogravimetric analysis of a DAD-type compound of the invention (X in FIG. 4) in air and in nitrogen atmospheres.

Example 6 describes a study in which the heat stability of DAD-type compound X (FIG. 2B) was assessed by thermogravimetric analysis. As can be seen from FIG. 9, when the compound was gradually heated in an air atmosphere, the compound did not begin to volatilize until a temperature of 375° C. was reached. In the presence of a nitrogen atmosphere, volatilization did not begin to occur until about 390° C., and 99% of the compound remained even after the temperature of 400° C. was reached.

This result illustrates the high stability of DAD compound X to heat, suggesting compatibility with the heating steps used in standard IC (integrated circuit) fabrication methods. More generally, this type of test provides a general idea of the susceptibility of a dipolar compound to heat-induced sublimation or decomposition.

Figure 12A:
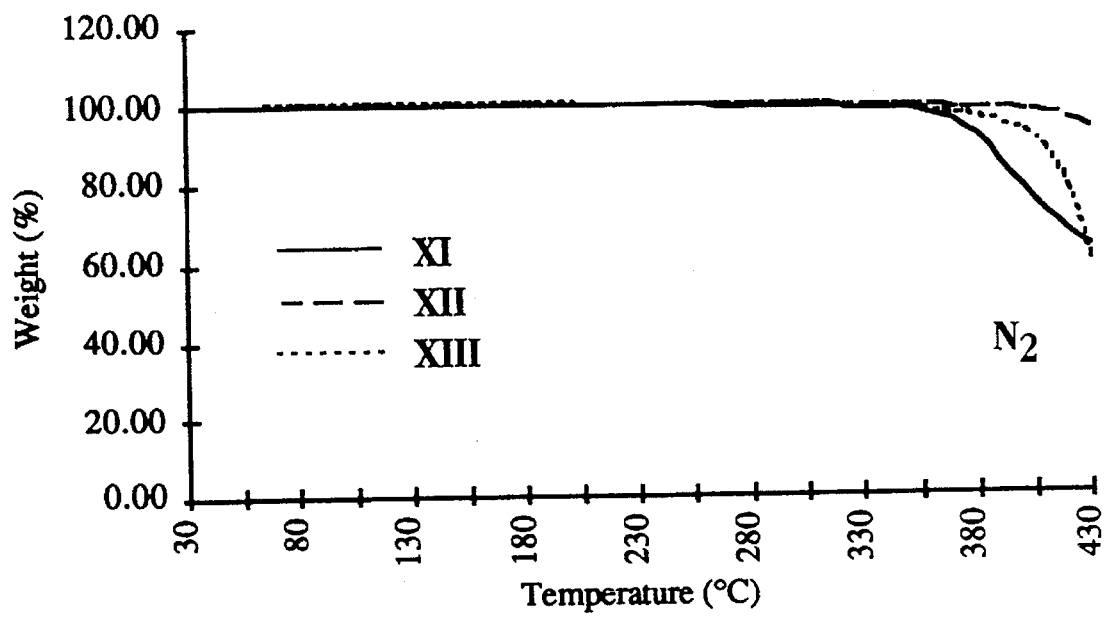
FIGS. 12A and 12B show thermogravimetric analyses of donor-acceptor-donor compounds wherein the donor groups are carbazole groups (compound XI), indole groups (compound XII), and 4-aminophenyl groups (compound XIII) in nitrogen atmosphere (FIG. 12A) and air (FIG. 12B).
Figure 12B:
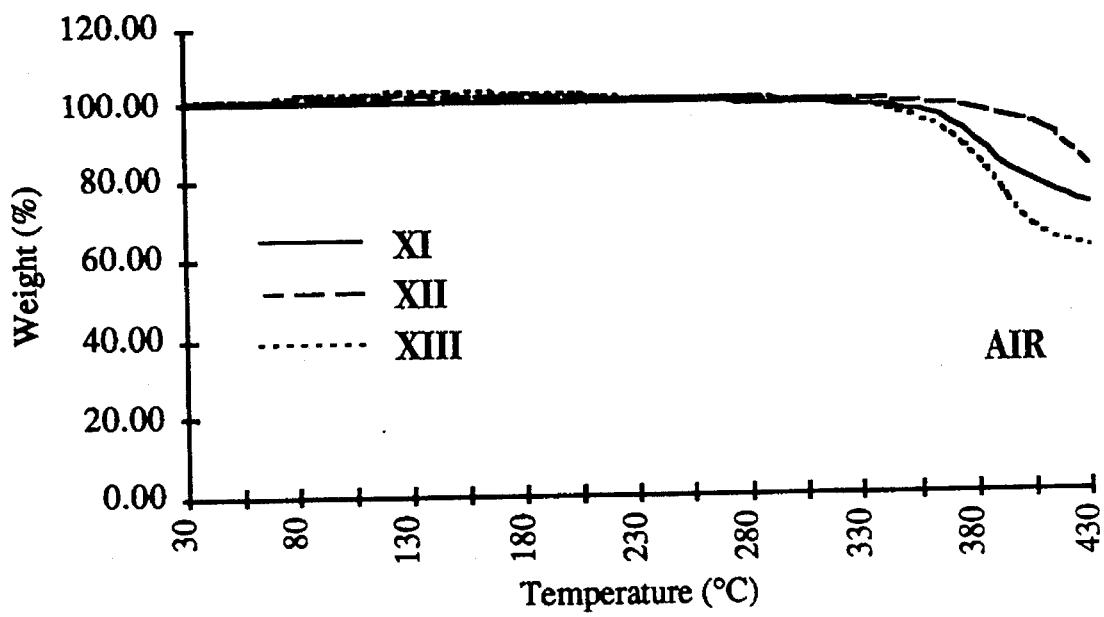

Thermogravimetric analyses of three additional compounds in accordance with the invention are shown in FIGS. 12A and 12B (compound XI corresponds to the structure in FIG. 2A, $R_1=R_2=$N-(n-hexyl)-3-carbazolyl; XII corresponds to FIG. 2A, $R_1=R_2=$N-(n-hexyl)-3-indolyl; and XIII corresponds to structure (c) above, n=m=2 and Y=H). As can be seen from the figures, all three compounds showed high thermal stabilities, both in air and in nitrogen atmospheres. In particular, for phenyl compound XIII, the onset of decomposition was 363° C. in air, and 372° C. in nitrogen atmosphere.

Example 7 details a study in which the mobility of a dipolar compound of the invention in a polyimide film matrix was examined by dielectric spectroscopy. The study involved a polyimide film containing 15 weight % of compound X, and for comparison, a similar film loaded with the dipolar compound "DCM" (4-(di-cyanomethylene)-

2-methyl-6-(p-dimethylaminostyryl)-4H-pyran; Ermer et al., 1992), which contains a single donor and single acceptor.

Figure 10:
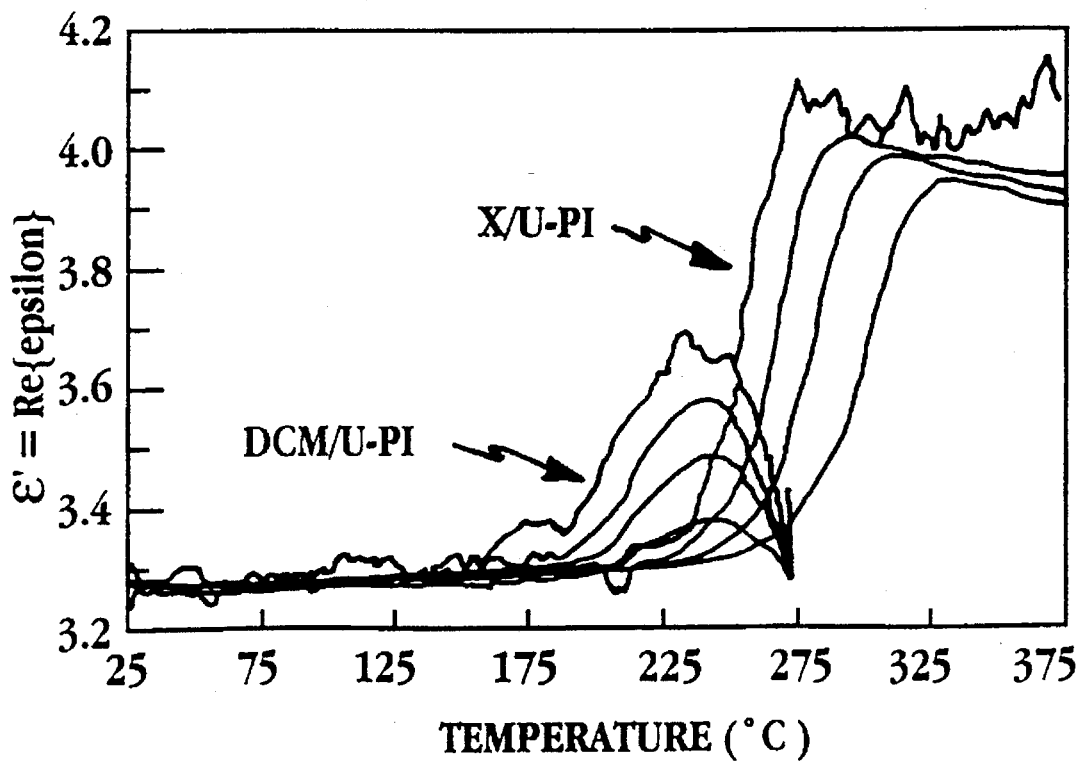
FIG. 10 shows dielectric spectra for a compound designated "DCM" ((4-(dicyanomethylene)-2-methyl-6-(p-dimethylaminostyryl-4H-pyran), and for compound X (FIG. 4)

With reference to FIG. 10, the DCM-containing matrix showed significant plasticization of the surrounding polymer matrix, that is, the glass transition temperature ($T_g$) of the matrix as a whole (~200° C.) was much lower than that of pure polymer matrix in the absence of added DCM. In addition, the return of the curve to a baseline value at about 275° C. indicates that much of the DCM had sublimed from the polymer matrix.

In contrast, the compound X-containing polymer showed a glass transition temperature of between about 260° and 300° C., much higher than that observed with the DCM compound.

These results show that the polymer matrix containing the DAD compound of the invention (X) is better able to resist relaxation of the net dipole in the polymer matrix than is a comparable matrix containing the DCM compound.

This type of study is also useful for establishing the temperature at which poling should be conducted. Specifically, the temperature at which $\epsilon'$ (the real part of the dielectric spectrum) begins to rise above baseline is a good starting point for the poling temperature used to induce a net dipole in matrices which contain the dipolar compound.

Figure 11:
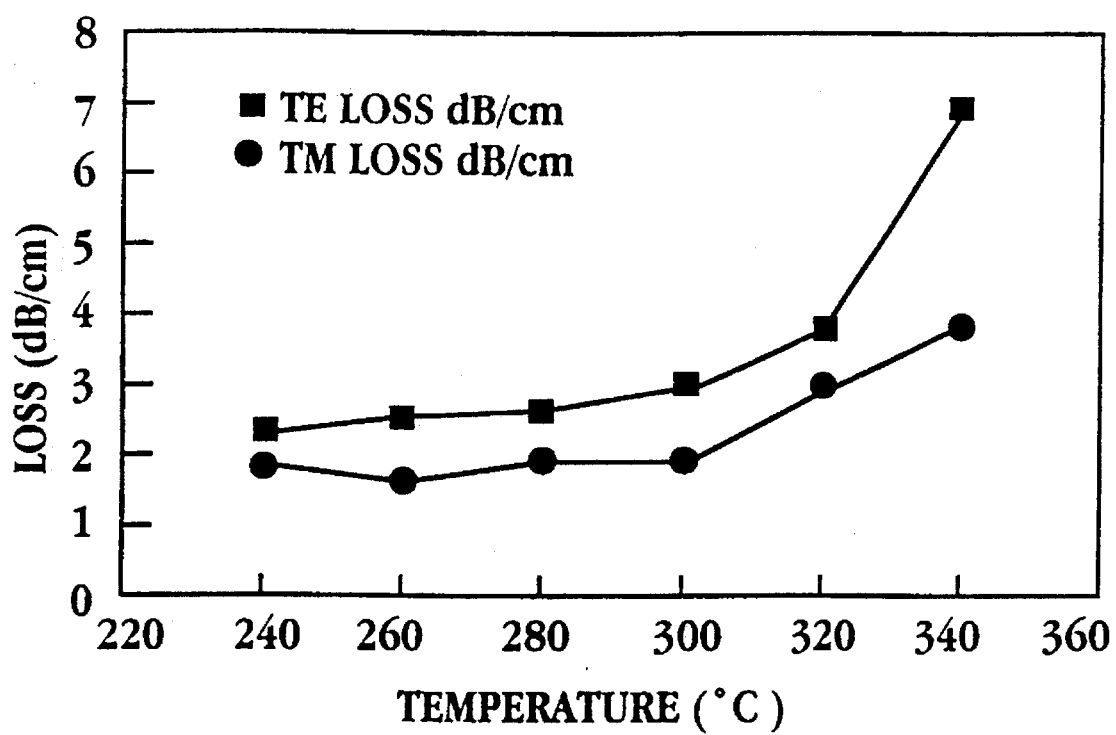
FIG. 11 shows a slab loss analysis of a polyimide polymer containing 15 weight % of compound X (FIG. 4)

Example 8 describes a study in which polyimide matrices containing different proportions of compound X were characterized for slab loss by the prism coupling technique. This method assesses optical loss due to light absorption and by scattering due to phase separation of guest (dipolar molecule) and host (polymer matrix). FIG. 11 shows that the slab loss was relatively low and constant until about 300° C. was reached. The increased loss at high temperature may be due to densification of the polyimide host, as is observed for the neat host material. This result shows that compound X has good light propagation properties at temperatures of about 300° C., and thus is compatible with the heating conditions used in IC fabrication.

A number of DAD-type compounds of the invention have also been characterized by electric-field induced second harmonic generation (EFISH), a technique which provides a measure of the magnitude of non-linear optical properties in a test compound.

The electronic origins of this phenomenon have been reviewed (Williams, D. J., *Angew. Chem. Int. Ed. Engl.* 23:690 (1984)). The method involves applying a strong DC electric filed to a solution of the compound of interest to remove orientational averaging by statistical alignment of molecular dipoles in the solution. The technique produces an emission signal at twice the frequency of the incident beam ($2\omega$), from which the hyperpolarizability parameter $\beta$ is calculated.

As can be seen from the results in Example 9, all of the compounds tested showed greater non-linearity than the standard reference compound, Disperse Red ($\beta$=70), indicating that the temperature-stable compounds of the invention exhibit high non-linearity.

III. Electro-Optic Waveguide Material

According to an important feature of the invention, the dipole compounds of the invention are useful in forming waveguide materials which are stable to the high temperatures typically used in IC fabrication and afford desirable electro-optic properties. The guest dipole molecules within the material are dissolved in a polymer matrix or, alternatively, are prepared as an integral part of the polymer matrix by copolymerization with linking subunits, by methods discussed above.

Although methods for preparing the waveguide material are illustrated below with respect to an embodiment in which the guest molecules are dissolved in the polymer matrix, it will be understood that the discussion applies to guest molecules covalently incorporated in the polymer matrix as well.

Figure 5:
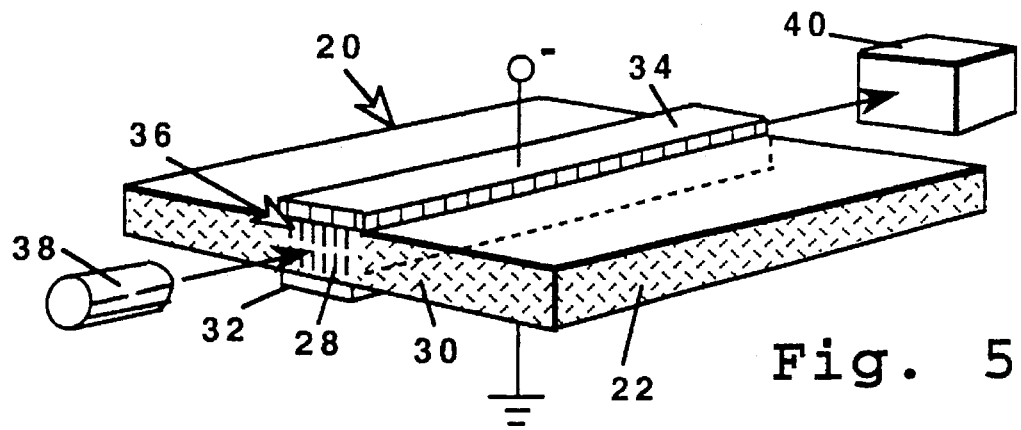
FIG. 5 is a perspective view of an electro-optic material constructed in accordance with the present invention, also showing electrodes used in generating an electric field across a region of the material.

FIG. 5 shows an electro-optic (EO) waveguide material 20 constructed according to one embodiment of the invention. The material is composed of a polymer matrix 22 of polymer chains, such as chains 24 seen in FIGS. 6A and 6B. The material has guest dipolar molecules, such as molecules 26 in FIGS. 6A and 6B, of the type described in Section II dissolved in the matrix. As noted above, the dipolar molecules may be of two types—acceptor-donor-acceptor (shown in FIGS. 6A and 6B) and donor-acceptor-donor. Considering the charge distribution in the molecules as having the general "Y" shape shown, the net dipole moment of a molecule would be directed substantially along the base of the Y, intersecting the two arms of the Y. In FIG. 5, the molecules are indicated by short lines, such as lines 28, 30, which represent the dipole moment vectors of the dipolar molecules in the material.

A. Formation of the EO Material

Polymer materials suitable for use in electrooptic devices are polymers that are optically transparent and chemically resistant to chemical treatments used in photoetching processing steps. In addition, preferred polymers are heat stable, meaning that the polymers can be baked to a high temperature, e.g., 250°–350° C. or higher without polymer decomposition. In addition, the polymers are preferably ones that can be cured under conditions leading to a high glass-transition temperature, e.g., above 250° C., and preferably between 300°–400°C.

It is useful, in understanding the thermal properties of the preferred polymers, to examine the behavior of the polymer matrix as it is cured and hardened by heating. Using polyimide as a preferred example, the polymer can be soft-baked at relatively low temperature, e.g., 150°–200° C., either in the presence or absence of vacuum, to remove polymer solvent, and to partially or completely imidize the polymer chains. At this stage the polymer should be sufficiently cured to resist solvent penetration, when subsequent polymer layers are formed over the polymer matrix, as described below for the fabrication of EO devices.

The polymer matrix may be cured at a higher temperature, e.g., 250°–350° C., to achieve a high degree of densification of the polymer matrix. The densified polymer may be quite heat stable at this point, but also may be sufficiently densified that it no longer has a glass transition temperature in a practical temperature range, or does not have sufficient mobility at its glass transition temperature to allow reorientation of the dipolar molecules in the matrix under the influence of an electric field.

After cooling, the cured or partially cured polymer may subsequently be brought to its glass transition temperature, at which the polymer chains are again mobile enough to allow dipolar molecules in the matrix to orient in the direction of an applied electric field. The glass transition temperature may be determined by dielectric spectroscopy, according to known methods (e.g., Example 7 and FIG. 10). Briefly, the dielectric constant of the material is measured over a given electric field frequency, typically between about 100 Hz and 100 KHz, as the material is brought through a series of temperature increases. At the glass-transition temperature, there is a sharp increase in the observed dielectric constant, due to the ability of the dipoles in the material to respond to the electric field frequency.

The glass transition temperature $T_g$ will depend both on the nature of the polymer chains and the curing conditions already applied to the material. In general, the $T_g$ will be at or above the curing temperature used in the initial curing procedure. As mentioned above, some polymers, including some polyimide polymers, will not exhibit sufficient mobility to allow for molecular orientation if they are cured to a point of extreme densification. Ideally, the initial curing conditions are between those sufficient, at the low temperature end, to prevent solvent penetration of subsequently added layers, and at the high temperature end, to cure the matrix to a temperature which still allows a $T_g$ to be reached below the range 325°–375° C. or somewhat less.

In examining the suitability and curing conditions of a given polymer for use in the present invention, it is useful to determine the polymerization and densification properties at desired heat-stability conditions, typically above about 250° C. Ideally, the polymer is one which can be cured and partially densified at baking temperatures between 255°–350° C., and still provide a $T_g$ in the range less than about 350°–375° C. at which molecular dipole orientation can occur in the presence of an applied electric field.

In the alternative, the polymer may be one which becomes highly densified in the temperature range 275°–350° C. This polymer may still be suitable if it has a suitable thermal stability after curing and baking at a high temperature, recognizing that the dipolar molecules will have to be oriented during the high-temperature baking step.

A final consideration in the thermal behavior of the polymer matrix is the ability to maintain its rigid polymer chain condition at elevated temperatures, e.g., in the range above 250° C. This is necessary in order to preserve the dipolar molecules in their oriented states at elevated temperature. Typically, this will be achieved by carrying out the final densification step and/or molecule poling step at a temperature above the desired thermal stability range, e.g., in the range 275°–400° C.

Polymers meeting the thermal stability criteria set out above include polyimides, typically supplied as polyamic acid or preimidized material in dried or solution form, such as Ultradel™ 3112, Ultradel™ 4212, Ultradel™ 9000D obtainable from Amoco (Naperville, Ill.), LQ2200™ obtainable from Hitachi (Japan), Pyralin™ obtainable from DuPont (Wilmington, Del.), and Probamide™ obtainable from OCG. Other thermally stable polymers which are suitable include polycarbonates, obtainable from a variety of polymer suppliers, such as Aldrich (Milwaukie, Wis.), polyurethanes, obtainable from a variety of polymer suppliers, such as Scientific Polymer Products (Ontario, N.Y.), polyquinolines, obtainable from Maxdem (San Dimas, Calif.), benzocyclobutene polymers, such as formed by polymerization of Cyclotene™ obtainable from Dow Chemical (Midland, Mich.), and polybenzoxazoles, obtainable from Daychem (Dayton, Ohio).

In formulating a polymer solution, the polymer chains are dissolved in a suitable solvent, such as N-methylpyrrolidone (NMP) or γ-butyrolactone, according to manufacturer's specifications, if the polymers are not already supplied in solution form. The solution is formulated for use in forming films, for example by spin or spray coating a silicon substrate or the like, according to standard IC fabrication methods. The dipolar molecules in the solution (Section II) are present in the polymer in an amount typically between about 5–35 percent by weight, and preferably 10–20 percent by weight of total solids (polymer and dipolar molecules).

After forming the polymer solution into a thin film, the material is cured or partially cured as discussed above. In one general embodiment, the polymer matrix is one which can be cured to a final cured state at a temperature above 250° C., and still provide a $T_g$ above the curing temperature that allows poling of the dipolar molecules, during a relatively brief high-temperature poling step.

In another general embodiment, the polymer matrix becomes highly densified in a final cured state, such that the poling step must take place as part of the final high-temperature curing step. In both embodiments, final curing at temperatures in the range 250°–325° C. or higher is desired, to ensure stability of the polymer at these temperatures.

Poling in the selected regions of the material is carried out by heating the polymer matrix above its $T_g$, or as part of a final curing step, and during the heating, applying an electric field across the material in the desired region of poling. The electric field is created by a pair of electrodes, at least one of which is shaped and dimensioned to correspond to the desired poled region. The poled region may include the entire polymer layer, or waveguide channel regions thereof, as discussed in Section IV.

In FIG. 5, the two electrodes are shown at 32, 34, connected, for example, to the negative side and ground, respectively of a voltage source. A poling voltage of between about 20–300 V/micrometer (μm) separation between electrodes, e.g., 50–100 V/μm, applied for a period of between about 0.5–5 minutes is sufficient to achieve desired molecular orientation, with higher melt temperatures above the $T_g$ requiring less poling time, when the material is above its glass transition temperature. For a polyimide polymer, the poling temperature is preferably between about 275°–350° C.

Alternatively, the poling may be performed as part of a final heat-curing step, e.g., where the matrix material is treated for example for 10–60 minutes at a temperature between 250°–350° C.

After poling, the material is cooled, with continued application of the electric field during cooling, to freeze the dipolar molecules in their oriented positions. During the cooling period, the polymer chains nest around the oriented molecules as the polymer cools, as evidenced by the stability of the oriented dipoles in the cooled material.

Figure 6A:
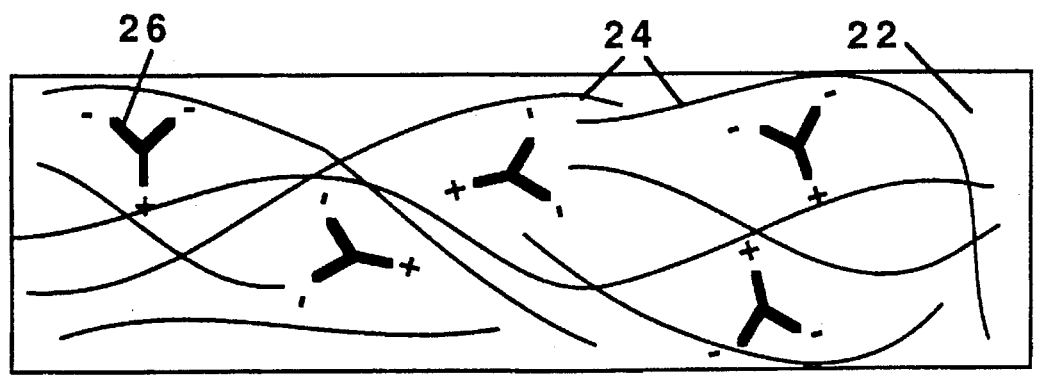
FIGS. 6A and 6B show regions of the electrooptic material in FIG. 5, before (6A) and after (6B) poling the material to align the guest molecule dipoles in the material.

As shown in FIG. 5 and FIG. 6A, the net dipoles of the molecules are substantially aligned with the direction of the electric field used in poling the molecules, and are immobilized within the free volume of the matrix.

Figure 6B:
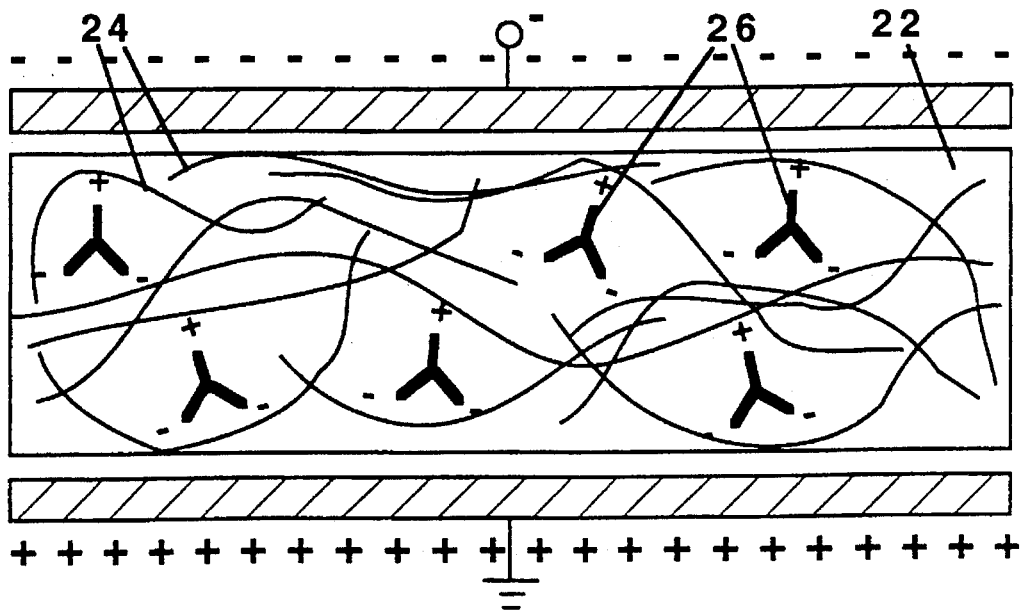

The molecular components of the material are shown diagrammatically in FIGS. 6A and 6B before and after poling, respectively. Before poling, the net dipole moments of the molecules, corresponding in direction to the base of the "Y" molecular shapes, have random orientations. The polymer chains may tend to be oriented in the direction of the plane of the material, as shown (Takahashi). After poling, the net dipole moments of the dipolar molecules are substantially aligned as indicated in FIG. 6B, with the polymer chains forming around the aligned molecules to freeze them into their aligned conditions.

B. Waveguide Operation

In order for the polymer material to guide modes of optical radiation, the polymer and the material adjacent to it (i.e., a buffer or cladding) must be transparent at the wavelength of the optical radiation, and the cladding must have a lower refractive index than the polymer and must be of sufficient thickness to prevent optical radiation in the polymer material from being significantly affected by any materials beyond the cladding. The modes of optical radiation that are guided by the polymer material in the absence of oriented dipolar molecules in the matrix are confined in only one dimension, namely the dimension perpendicular to the plane of the material. The guided modes are not confined in either lateral dimension.

In the embodiment shown, the waveguide channel, indicated at 36, is formed by the region of oriented dipolar compounds, and the lateral cladding by adjacent non-channel regions of the material in which the dipolar molecules are randomly oriented. In addition, the dipole molecules in non-channel regions of the material can be photobleached, as described below, to further reduce the index of refraction of the non-channel regions.

In still another embodiment, also described below, portions of the waveguide channel may contain passive waveguide regions of non-oriented dipolar molecules, and switching regions of oriented dipolar molecules, where non-channel regions of the material contain photobleached molecules or polymer lacking dipolar molecules.

More generally, the EO material contains a waveguide channel having at least regions in which the dipolar molecules have a dominant orientation, preferably with the net dipole moments oriented normal to the plane of the material, as shown in FIG. 6B.

Considering the operation of the EO material, it is assumed that the section of EO material shown in FIG. 5 corresponds to a switch region in the layer of an EO device of the type to be described in Section IV below. That is, the waveguide channel 36 shown in the figure is part of an elongate channel which includes channel regions both upstream of the switch region, which receives light signals from a laser source 38, and downstream of the switch region, where the light signals are processed by a photosensing device 40.

The poled channel portion shown in FIG. 5 has a greater index of refraction than does the adjacent non-channel portions for at least one polarization of the optical radiation. A beam of optical radiation from a source is thereby confined within the lateral dimension of the channel which therefore, in combination with the lateral non-channel regions, and upper and lower cladding (not shown) functions as an optical waveguide. The phase of a beam of optical radiation propagated through channel 36 can be modulated by placing switching electrodes across the channel section. The switching electrodes, here electrodes 32, 34, are spaced apart from the channel waveguide by cladding portions of the polymer material, or by cladding layers formed over the waveguide channel, as described below.

Because of the linear EO effect, the application of a modulating electric field across the channel by the switching electrodes changes the refractive index of the channel in the region where the field is applied. Little or no reorientation of the dipolar compounds is produced by the modulating electric field, since the host polymer of waveguide material is quite immobilized and in any case the electric field applied during operation of an EO device is much smaller than that used in poling the dipolar molecules.

The increase in the refractive index of the waveguide channel imparts a phase shift to the beam of optical radiation propagating through the switching region. The phase shift may be used to produce a desired EO switching effect in an EO device of the general type described below.

IV. Electro-Optical Devices

Three-dimensional waveguides, both active (electro-optic) and passive, which confine guided modes of optical radiation in two dimensions are essential components of integrated electro-optic devices. By partially orienting, or "poling", the optically active dipolar moieties in a selected region or regions of a polymer material layer, such as described in Section III, a network of three-dimensional electro-optic (EO) waveguides can be formed in the polymer layer in a single process.

Figure 7A:
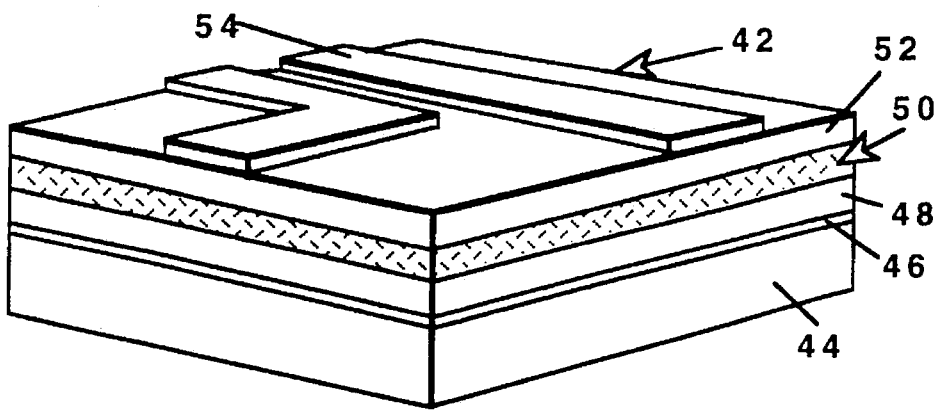
FIGS. 7A–7C illustrate steps in forming an electro-optic device in accordance with one embodiment of the invention.
Figure 7B:
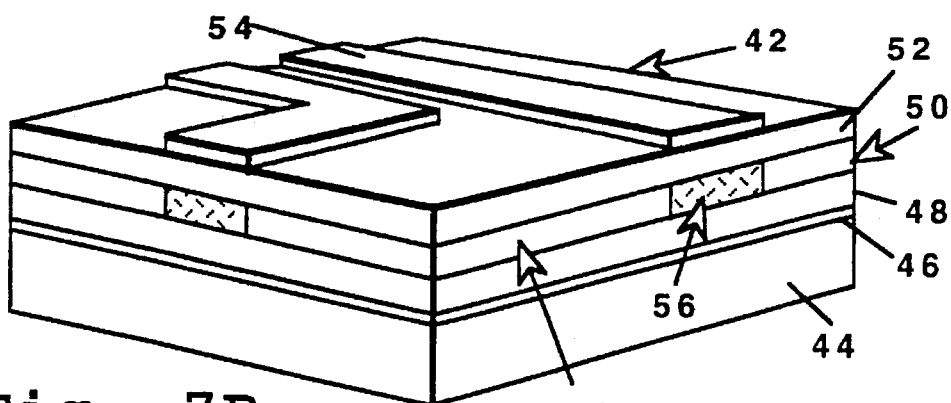
Figure 7C:
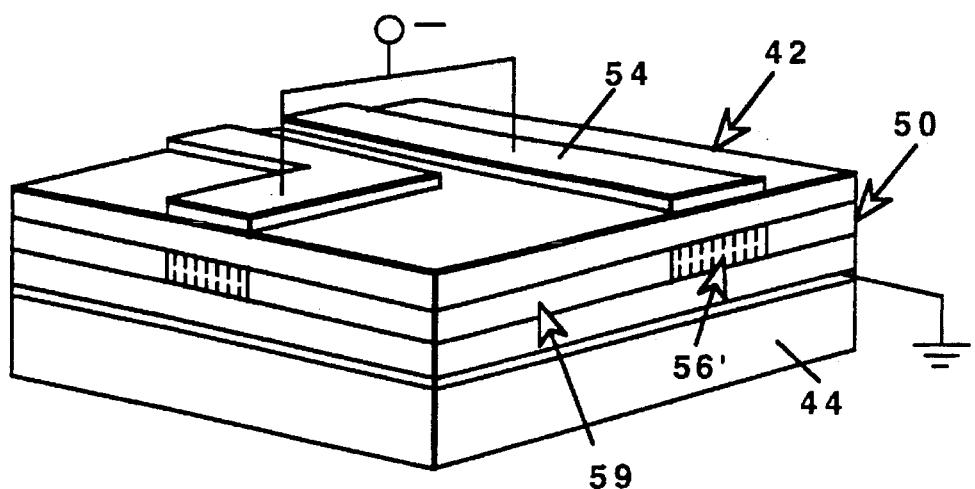

One method for fabricating an electro-optic device in accordance with the present invention is illustrated in FIGS. 7A–7C. FIG. 7A shows a section of a waveguide block 42 for use in forming a waveguide in an EO device, in accordance with the invention. The waveguide is fabricated by forming on a suitable substrate 44, such as a silicon substrate, an electrode film 46, and successive layers which include a lower cladding layer 48, a core EO layer 50, and an upper cladding layer 52. The polymer material forming the core layer has the polymer and dipolar molecule composition described in Section III. The two cladding layers 48, 52 are composed of a polyimide or other heat-stable polymer of the type described above, preferably similar or the same polymer used in the core layer.

The polymer and electrode layers are deposited using conventional IC manufacturing equipment. After each polymer layer is deposited, the new layer is cured, at least partially, as described above. A final electrode configuration, including electrode 54 is formed on the upper layer of the block, and corresponds to the shape and dimensions of the desired waveguide channel.

To form the waveguide channel(s), the block is photobleached using the electrodes as a photomask. Photobleaching may be carried with a conventional UV light source, such as a mercury lamp, at a total exposure of between 100–500 J/cm$^2$. As indicated in FIG. 7B, the photobleaching is effective to form waveguide channel regions, such as region 56 containing unbleached molecules, and non-channel regions, such as region 58, containing bleached molecules which now serve as lateral cladding for the channels. The photobleaching may alternatively be carried out prior to forming the upper electrodes, using an IC photomask. In the final step, the block is poled, as described above, to align the dipole moments in the waveguide channels as indicated. The poled channels, such as channel 56', are EO channels which may be employed as passive waveguide channels or active EO switching elements in the EO device.

As discussed above, the poling step is preferably carried out after the block is first fully cured at a temperature above 250° C. At this stage, the block is heated to its $T_g$, preferably between 275° and 350° C., then poled by application of an electric field across the upper electrodes, such as electrode 54, and lower electrode plate 46. After poling, and with continued application of the electric field, the block is cooled to freeze the dipolar molecules in their oriented positions in the matrix. As shown in FIG. 7C, the waveguide channels, such as channel 56' defined by unbleached dipolar molecules have oriented dipoles which allow EO switching with the application of electric fields across the channels.

Collectively, the lower cladding layer, core layer, and upper cladding layer form an EO waveguide 59 having waveguide channels, such as shown at 56', with oriented dipoles. The polymer and dipolar molecules forming the channels have the composition and characteristics described in Sections II and III above.

Figure 8A:
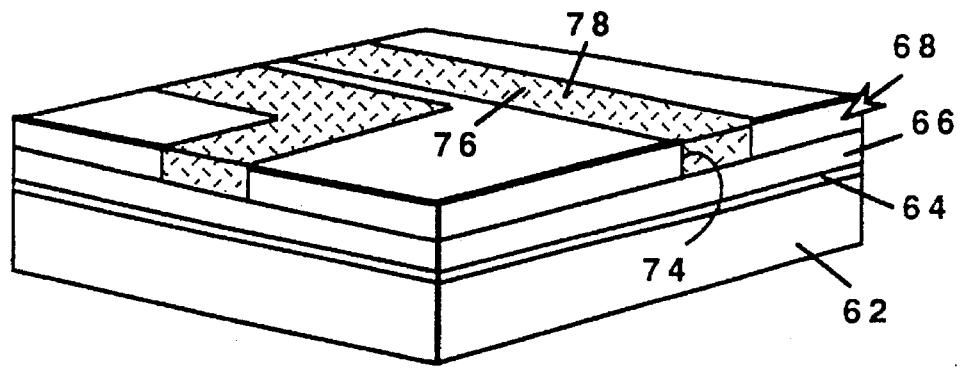
FIGS. 8A–8C illustrate steps in forming an electro-optic device in accordance with another embodiment of the invention.
Figure 8B:
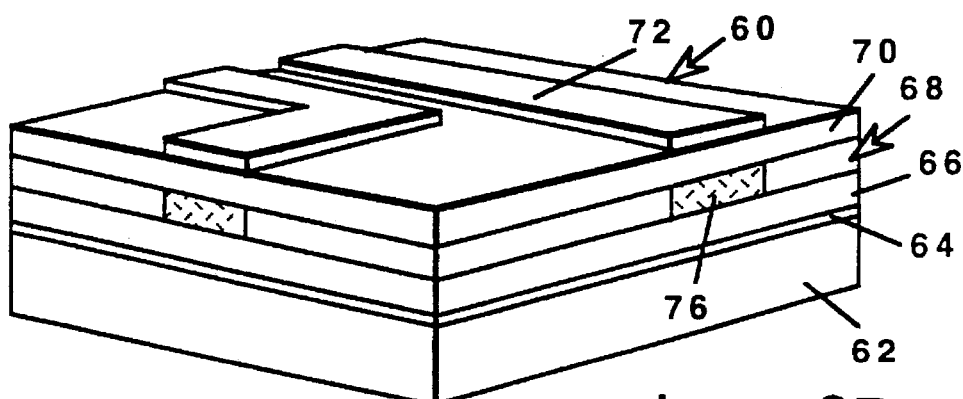

FIGS. 8A–8B illustrate another general method for forming an EO device in accordance with the invention. FIGS. 8A and 8B illustrate the formation of a block 60 forming a section of an EO device. With reference to FIG. 8B, the block includes a substrate 62, an electrode layer 64, and successive layers which include a lower cladding layer 66, a core EO layer 68, and an upper cladding layer 70. An electrode pattern, including an electrode 72, is formed on the upper block surface.

The three polymer layers in block 60 are similar to layers 48, 50, 52, described with respect to FIGS. 7A–7C, except that in core layer 68, the polymer material containing dipolar molecules is confined to the waveguide channels in the core layer. Specifically, and as seen in FIG. 7A, the core layer is made by first forming on the lower cladding layer, a core polymer layer which is composed of polymer alone, that is, a polymer solution which does not contain dipolar molecules.

This layer, after curing, is etched, such as by conventional photoetching techniques, to form channels, such as channel 76, which will form the waveguide channels in the device. The channels are then filled with polymer material, such as indicated at 78, containing a polymer matrix and dipolar molecules in accordance with the material described in Section III, and the material is partially or completely cured, as above, with the dipolar molecules in a randomly ordered condition.

Figure 8C:
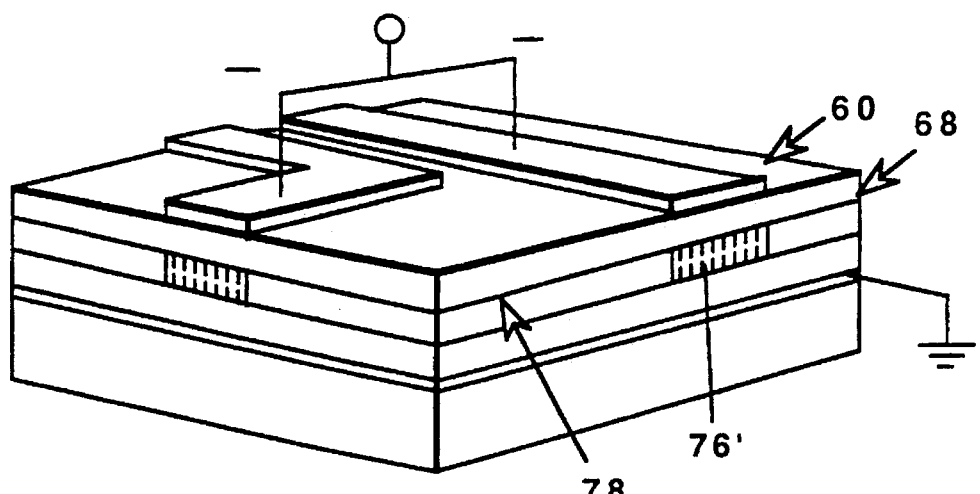

The upper cladding layer and electrodes are then formed over the core layer, to complete the block, shown in FIG. 8B. In the final step, the block is heated to above the $T_g$ of the core layer, and at least to 250° C., and the dipolar molecules in the core-layer channels are poled by application of an electric field across the upper and lower electrodes in the block, to produce EO waveguide channels, such as channel 76', with oriented dipolar molecules, as seen in FIG. 8C.

As above, the lower cladding layer, core layer, and upper cladding layer form an EO waveguide 78 having waveguide channels, such as channel 76', with oriented dipoles, where the polymer and dipolar molecules forming the channels have the composition and characteristics described in Sections II and III above.

The fabrication methods just described are used to construct EO device, such as an optical rail tap (Van Eck) and a Mach-Zender modulator (Girton).

The technique of the present invention using thermally stable dipolar compounds has several advantages. One advantage is the ability to heat the device to processing temperatures up to approximately 350° C. while maintaining the structural integrity of the guest dipolar compounds. Thus, a wider range of polymer host material can be selected, as the maximum processing temperature is increased. In addition, forming a network of EO channel waveguides by a single process is advantageous over other procedures for fabricating organic EO waveguide devices, because the overall device fabrication process is simplified.

The following examples illustrate various synthetic and analytical approaches used in the invention and are intended to illustrate but not limit the invention.

EXAMPLES

Experimental

All organic chemicals were purchased from Aldrich Chemical Company except as noted and were used as received.

Melting points (mp) were determined in capillary tubes on a Mel-Temp II capillary melting point apparatus using a digital thermometer and are uncorrected.

Proton nuclear magnetic resonance ($^1$H NMR) spectra were obtained at room temperature (RT) on a Varian XL-300 NMR spectrometer using deuteriochloroform (CDCl$_3$) as solvent and tetramethylsilane (TMS) as internal standard, unless otherwise indicated. Chemical shifts are reported in parts per million (ppm).

Fourier transform infrared (FT-IR) spectra were measured on a KVB/Analect RFX300 FT-IR spectrometer. Ultraviolet-visible (UV-vis) spectra were obtained on a Varian Cary 5E spectrometer.

Elemental microanalyses were performed by Desert Analytics (Tucson, Ariz.).

Example 1

Synthesis of ADA Compound VII 3,6-Bis(2-(3-(1-dicyanomethylidene-5,5-dimethylcyclohex-2-enyl))-ethenyl)-9-ethyl-9H-carbazole To a solution of isophorone (1.2 mL, 7.7 mmol) in DMF (8 mL) was added malononitrile (0.44 mL, 7.7 mmol), followed by 10 drops of acetic acid, 7 drops acetic anhydride, and 0.3 mL piperidine. The color of the resultant solution changed from orange to dark red during addition of the piperidine. The mixture was stirred for 1 hour at RT, and then 1 hour at 80° C. 9-Ethyl-9H-carbazole-3,6-dicarboxaldehyde (VI, 0.85 g, 3.4 mmol) was then added to the reaction mixture, and the resultant solution was stirred overnight at 80° C.

The reaction solution was cooled to RT and poured into 150 mL water. The resultant solid was filtered, air-dried, dissolved in dichloromethane, and passed through a short column of silica gel. Product-containing eluant was collected and roto-evaporated, and the residue was recrystallized from chloroform/ethyl acetate to give 0.36 g of product (VII) as a red solid (18% yield): mp 308.6°–310° C.

Example 2

Synthesis of Dicarbazole DAD Compounds

A. (2,6-Bis(2-(3-(9-(ethyl)carbazolyl))ethenyl)-4H-pyran-4-ylidene)propanedinitrile (X).

A solution of 9-ethyl-9H-carbazole-3-carboxaldehyde (10.00 g, 44.8 mmol), (2,6-dimethyl-4H-pyran-4-ylidene)propanedinitrile (3.86 g, 22.4 mmol), and piperidine (2 mL) in toluene (100 mL) was refluxed overnight using a Dean-Stark apparatus. The reaction solution was cooled to RT, and the solvent was roto-evaporated. The resultant crude solid was recrystallized twice from N,N-dimethylformamide/ethyl acetate to give the product as an orange solid, 1.39 g (11%): mp 337.6°–338.4° C.; $^1$H NMR (CDCl$_3$) δ1.52 (t, J=7.1 Hz, 6H, two CH$_2$C$\underline{H}_3$), 4.46 (q, J=7.1 Hz, 4H, two C$\underline{H}_2$CH$_3$), and 6.67–8.37 (m, 20H, fourteen aromatic H and six other CH); FT-IR (KBr) 2203 and 2188 cm$^{-1}$ (CN stretch); UV-vis, $\lambda_{max}$ (NMP) 459 nm ($\epsilon$=7.10×10$^4$); Anal. Calcd. for C$_{40}$H$_{30}$N$_4$O: C, 82.45; H, 5.19; N, 9.61. Found: C, 82.34; N, 4.98; N, 9.34.

B. 2,6-Bis(2-(9-hexyl-9H-carbazol-3-yl)ethenyl)-4H-pyran-4-ylid ene)propanedinitrile (XI)

A solution of 9-hexyl-3-carbazolecarboxaldehyde (3.76 g, 13.4 mmol), (2,6-dimethyl-4H-pyran-4-ylidene)propanedinitrile (1.15 g, 6.7 mmol), and piperidine (2 mL) in toluene (25 mL) was refluxed overnight using a Dean-Stark trap. The reaction solution was then cooled to room temperature, and the precipitated crude solid was filtered and recrystallized from toluene to give product (1.63 g, 35% yield) as dark orange crystals: mp 226.4°–226.9° C.; 1H NMR (CDCl$_3$) δ0.88 (t, J=6.5 Hz, 6H, two CH$_3$), 1.23–1.46 (m, 12H, aliphatic CH$_2$), 1.82–1.94 (m, 4H, aliphatic CH$_2$), 4.31 (t, J=7.2 Hz, 4H, two NCH$_2$), 6.49 (s, 2H, two pyran ring CH), 6.69 and 7.67 (two d, J=16 Hz, 2H each, four trans double bond CH), 7.28–8.28 (m, 14H, aromatic H); FT-IR (KBr) 2206 cm$^{-1}$ (CN stretch); UV-vis λmax (NMP) 460 nm (ε=6.98×10$^4$); Anal. Calcd for C$_{48}$H$_{46}$N$_4$: C, 82.97; H, 6.67; N, 8.06. Found: C, 82.58; H, 6.52; N, 8.29.

Example 3

Synthesis of Diindole DAD Compound
(2,6-Bis(2-(1-hexylindol-3-yl)ethenyl)-
4H-pyran-4-ylidene)propanedinitrile (XII)

A solution of 1-hexyl-3-indolecarboxaldehyde (0.80 g, 3.47 mmol), (2,6-dimethyl-4H-pyran-4-ylidene)propanedinitrile (0.30 g, 1.74 mmol), and piperidine (1 mL) in toluene (25 mL) was refluxed for 5 hours using a Dean-Stark trap. The reaction solution was cooled to RT, roto-evaporated, redissolved in dichloromethane, passed through a short bed of silica, and roto-evaporated again. The resulting solid was recrystallized from toluene to give the product as a red crystalline solid, 0.64 g (62%): mp 194.3°–195° C.; $^1$H NMR (CDCl$_3$) δ0.91 (t, J=6 Hz, 6H, two CH$_3$), 1.26–1.44 (m, 12H, aliphatic CH$_2$), 1.85–1.98 (m, 4H, two NCH$_2$C$\underline{H}_2$), 4.20 (t, J=7 Hz, 4H, two NCH$_2$), 6.57 (s, 2H, two cyclohexene ring CH), 6.72 (d, J=16 Hz, 2H, two trans double bond CH), 7.30–7.47 (m, 6H, aromatic H), 7.52 (s, 2H, two indole ring C2 H), 7.76 (d, J=16 Hz, 2H, two trans double bond CH), 7.98 (dd, J=6.3 and 2 Hz, 2H, aromatic H); FT-IR (KBr) 2203 cm$^{-1}$ (CN stretch); UV-vis λmax (NMP) 466 nm (ε=6.22×10$^4$); Anal. Calcd for C$_{40}$H$_{42}$N$_4$O: C, 80.78; H, 7.11; N, 9.42. Found: C, 80.47; H, 6.90; N, 9.25.

Example 4

Synthesis of Diphenyl DAD Compound
(2,6-Bis(2-(4-(ethyl(2-
hydroxyethyl)amino)phenyl)ethenyl)-4H-
pyran-4-ylidene)-propanedinitrile (XIII)

A solution of 4-(ethyl (2-hydroxyethyl)amino)benzaldehyde (3.43 g, 17.8 mmol), (2,6-dimethyl-4H-pyran-4-ylidene)propanedinitrile (1.53 g, 8.89 mmol), piperidine (2 mL), and glacial acetic acid (1 mL) in toluene (100 mL) was refluxed overnight using a Dean-Stark trap. The reaction solution was cooled to RT, and the solvent was roto-evaporated. Flash chromatography (9:1 dichloromethane:ethyl acetate) and recrystallization from toluene gave the product as a dark brown powder, 0.75 g (16%): mp 222.5°–224.5° C.; $^1$H NMR (CDCl$_3$) δ1.20 (t, J=6.8 Hz, 6H, two NCH$_2$C$\underline{H}_3$), 1.74 (t, J=5.5 Hz, 2H, two OH), 3.49 (q, J=6.8 Hz, 4H, two NC$\underline{H}_2$CH$_3$), 3.54 (t, J=5.9 Hz, 4H, two NC$\underline{H}_2$CH$_2$OH), 3.83 (dt, J=5.5 and 5.9 Hz, 4H, two NCH$_2$C$\underline{H}_2$OH), 6.43 and 7.41 (two d, J=15.5 Hz, 2H each, trans double bond CH), 6.49 (s, 2H, two cyclohexene ring CH), 6.74 and 7.41 (two d, J=8.7 Hz, 4H each, aromatic H); FT-IR (KBr) 2204 and 2189 cm$^{-1}$ (CN stretch); UV-vis λmax (NMP) 499 nm (ε=7.05×10$^4$); Anal. Calcd for C$_{32}$H$_{34}$N$_4$O$_3$: C, 73.54; H, 6.56; N, 10.72. Found: C, 73.08; H, 6.42; N, 10.54.

Example 5

Synthesis of Dithiophene DAD Compounds

A. (2,6-Bis(2-(5-(1-pyrrolidinyl)thien-2-yl)ethenyl)-
4H-pyran-4-ylidene) propanedinitrile (XIV)

A solution of 5-(1-pyrrolidinyl)-2-thiophenecarboxaldehyde (1.45 g, 8.00 mmol), (2-6-dimethyl-4H-pyran-4-ylidene)propanedinitrile (0.69 g, 4.00 mmol), piperidine (2 mL), and glacial acetic acid (1 mL) in benzene (100 mL) was refluxed overnight under argon using a Dean-Stark trap. The reaction mixture was cooled to room temperature (RT) and filtered. The crude product was washed with benzene, then recrystallized from N,N-dimethylformamide (DMF) to give the product as brown crystals, 1.14 g (57%): mp >350° C.; FT-IR (KBr) 2180 and 2196 cm$^{-1}$ (CN stretch); UV-visλ$_{max}$ (NMP) 603 nm (ε=4.75×10$^4$), 529 nm (ε=6.33×10$^4$), 432 nm (ε=2.46×10$^4$); Anal. Calc. for C$_{28}$H$_{26}$N$_4$S$_2$: C, 67.44; H, 5.26; N, 11.24; S, 12.86. Found: C, 67.34; H, 5.38; N, 11.42; S, 12.62.

B. 2-6-Bis(2-(5-(dibutylamino)thien-2-yl)ethenyl)-
4H-pyran-4-ylidene)propanedinitrile (XV)

A solution of 5-dibutylamino-2-thiophenecarboxaldehyde (1.38 g, 5.76 mmol) (prepared from 5-bromo-2-thiophenecarboxaldehyde, dibutylamine, anhydrous potassium carbonate, and "ALIQUAT" 336 (Aldrich Chem. Co.) in dimethyl sulfoxide (DMSO) at 110° C. for three days), (2,6-dimethyl-4H-pyran-4-ylidene)propanedinitrile (0.4976 g, 2.89 mmol), piperidine (2 mL), and glacial acetic acid (1 mL) in benzene (100 mL) was refluxed for 22 hours using a Dean-Stark trap. The reaction solution was cooled to room temperature (RT) and roto-evaporated. Hexane was added to the solid which was filtered and re-dissolved in dichloromethane. The organic solution was washed with water and brine, dried with anhydrous magnesium sulfate, filtered through a short bed of flash silica gel, and roto-evaporated. The crude solid was recrystallized from ethyl acetate/hexane to give the product as green crystals, 1.12 g (64%): mp 209°–210° C.; $^1$H NMR (DMF-d$_7$) δ0.96 (t, J=7.1 Hz, 12H, four CH$_3$), 1.31–1.45 and 1.61–1.72 (two m, 8H each, eight aliphatic CH$_2$), 3.42 (t, J=7.3 Hz, 8H, four NCH$_2$) 6.06 and 7.28 (two d, J=4.2 Hz, 2H each, four thiophene ring CH), 6.41 and 7.89 (two d, J=15.4 Hz, 2H each, four trans double bond CH), 6.58 (s, 2H, two pyran ring CH); FT-IR (KBr) 2192 and 2177 cm$^{-1}$ (CN stretch); UV-vis λ$_{max}$ (NMP) 434 nm (ε=2.68×10$^4$), 533 nm (ε=6.96×10$^4$), 608 nm (ε=5.22×10$^4$); Anal. Calc. for C$_{36}$H$_{46}$N$_4$OS$_2$: C, 70.32; H, 7.54; N, 9.11; S, 10.43. Found: C, 70.21; H, 7.57; N, 9.03; S, 10.50.

Example 6

Thermal Stability of Compounds

The thermal stability of compound X (Example 2) was assessed by thermogravimetric (TGA) analysis using a Dupont TGA 2950 system. Compound X was heated at 20° C./min in a nitrogen or air atmosphere, and the weight of the compound was recorded over time. As can be seen from FIG. 9, the onset of weight loss in air occurred at 375° C. Under nitrogen atmosphere, a minor weight loss began to occur at about 389° C., but 99% of the original weight was still present at 400° C., the upper temperature limit of the run. Similar results obtained with DAD compounds XI, XII, and XIII are discussed above with reference to FIGS. 12A and 12B.

Example 7

Temperature-Dependence of Dielectric Constant

The temperature dependence of the dielectric spectrum of compound X in a polyimide host was determined as follows. To 75 g of Amoco Ultradel™ 3112 (polyimide host, ~11.5 weight % in N-methylpyrrolidinone, "NMP") was added 1.5 g of X (Example 2), and the mixture was agitated for 3 hours at RT. The mixture was then spun to form a film (Boyd, 1980; McCrum, 1967) for analysis. For comparison, a mixture of DCM (4-(dicyanomethylene)-2-methyl-6-(p-dimethylaminostyryl)- 4H-pyran; Ermer et al., 1992) in Amoco Ultradel™ 3112 was also prepared.

FIG. 10 shows the real part of dielectric spectra of the films containing X and DCM, recorded at frequencies (v) of 0.1, 1, 10, and 100 kHz (left to right). With reference to the curves labeled "DCM" in the figure, the position of the alpha transition of those curves indicates that the host is plasticized significantly by the DCM compound. Moreover, above 275° C., the spectrum becomes identical to that of pure polyimide host, presumably due to sublimation.

In contrast, the polyimide mixture containing compound X showed a glass transition temperature of between about 260° and 300° C., depending on the field frequency. No sublimation was observed, however, even at 375° C.

Example 8

Temperature-Dependence of Slab Loss

The effect of temperature on slab loss was determined for polyimide mixtures containing compound X by the prism coupling technique. Polyimide mixtures containing various weight percentages of compound X (5–15 weight %) were prepared as in Example 7, and deposited as films on $SiO_2$ wafers for slab loss measurements. The films were 3 μm thick and were cured at temperature of about 240° to 340° C. Slab loss was determined as a function of temperature by monitoring the lowest order mode losses at 830 nm by prism coupling.

The results for a polyimide mixture containing by weight of compound X are shown in FIG. 11. As can be seen, slab loss was minimal at temperatures of up to about 300° C. The increased loss at higher temperature may be due to densification of the polyimide host, as is observed in the absence of compound X.

Example 9

EFISH Measurements for DAD Compounds

Standard EFISH measurements on selected compounds were performed in chloroform solvent using a 1.907 μm laser light beam. The results are shown in Table 1 below.

TABLE 1

| Compound | μ(D) | $\beta_{1.907}$ ($10^{-30}$ esu) | $\mu\beta_{1.907}$ ($10^{-30}$ esu-D) |
|---|---|---|---|
| XIII | 12.6 | 197 | 2480 |
| XV | 13.1 | 215 | 2830 |
| XI | 10.7 | 106 | 1130 |
| XII | 11.9 | 70.8 | 842 |

Although the invention has been described with respect to particular dipolar compounds and devices, it will be apparent various changes and modifications can be made without departing from the invention.

It is claimed:

1. A heat-stable electro-optic waveguide material comprising guest dipole subunits having a structure selected from the group consisting of:

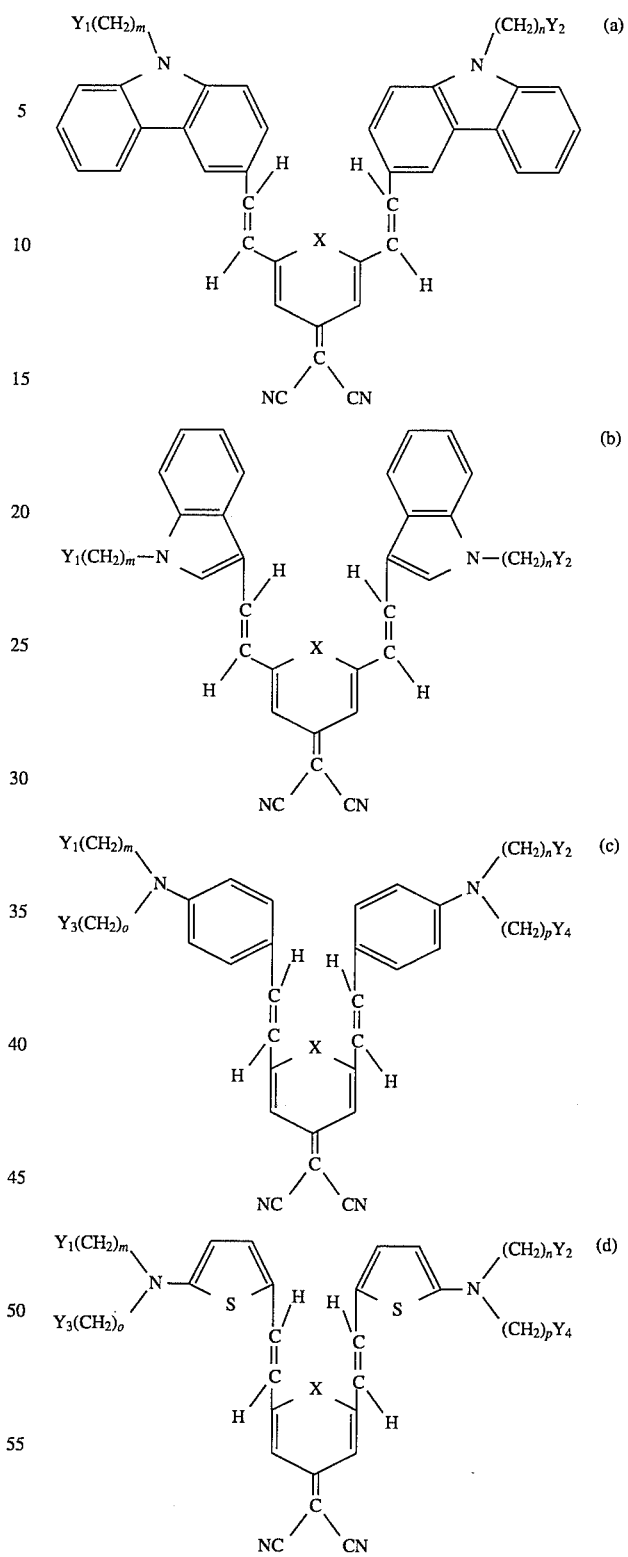

wherein X is O, S, $CH_2$, or NR, where R is a lower alkyl group; $Y_1$, $Y_2$, $Y_3$ and $Y_4$ are separately H, OH, or OL where L is a polymer linker subunit, and at least one of $Y_1$ and $Y_2$ is OL; and m, n, o and p are separately integers from 2 to 7.

2. The electro-optic waveguide material of claim 1, wherein X is O.

3. The electro-optic waveguide material of claim 2, wherein the guest dipole subunits have the structure shown at (a).

4. The electro-optic waveguide material of claim 2, wherein the guest dipole subunits have the structure shown at (b).

5. The electro-optic waveguide material of claim 2, wherein the guest dipole subunits have the structure shown at (c).

6. The electro-optic waveguide material of claim 2, wherein the guest dipole subunits have the structure shown at (d).

7. The waveguide material of claim 2, which contains non-waveguide regions in which the guest dipole subunits are photobleached.

8. The waveguide material of claim 2, which is substantially planar, and wherein the net dipole moments of the guest dipole subunits have a net orientation that is normal to the plane of the material.

9. The waveguide material of claim 1, wherein X is S.

10. An electro-optic waveguide material comprising a heat-stable polymer matrix having dissolved therein, guest dipole molecules having one of the general forms:

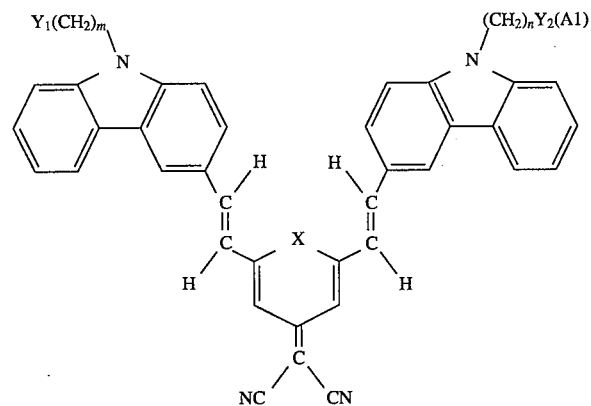
(A1)

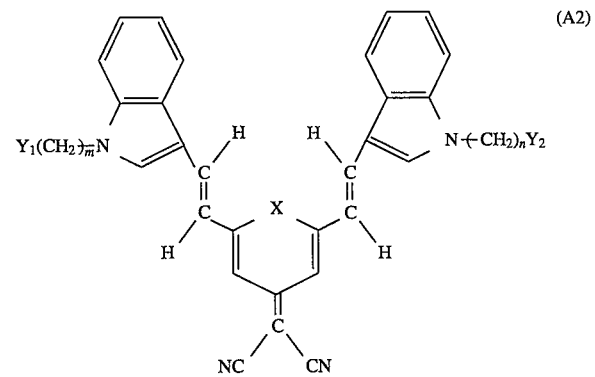
(A2)

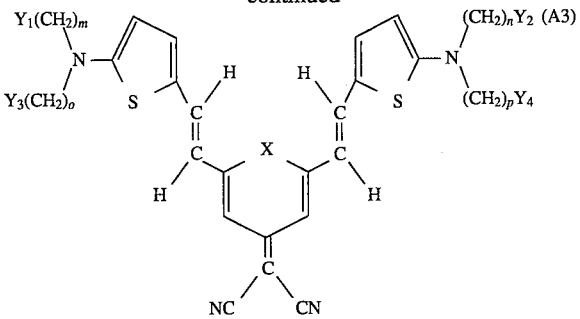
(A3)

wherein X is O, S, $CH_2$, or NR, where R is a lower alkyl group; $Y_1$, $Y_2$, $Y_3$ and $Y_4$ are separately H or OH; and m, n, o and p are separately integers from 2 to 7; or $Y_1$ and $Y_3$ taken together are —$CH_2CH_2$—, forming a cyclic amine wherein the sum of m+o is an integer from 0 to 2, and $Y_2$ and $Y_4$ taken together are —$CH_2CH_2$—, forming a cyclic amine wherein the sum of n+p is an integer from 0 to 2; or

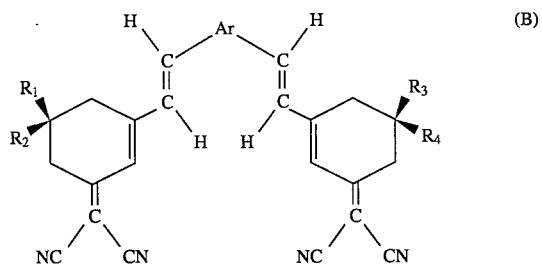
(B)

wherein Ar is an aromatic fused ring structure having a ring-contained tertiary amine, and $R_1$, $R_2$, $R_3$, and $R_4$ are the same or different and are each selected from the group consisting of H, an alkyl group or substituted alkyl group, the guest molecules having net dipole moments which are oriented in regions of the material such that the index of refraction of said regions can be modulated for optical switching purposes by applying an electric field across the regions.

11. The waveguide material of claim 10, which contains non-waveguide regions in which such guest dipole molecules are photobleached.

12. The waveguide material of claim 10, which is substantially planar, and wherein the net dipole moments of the guest molecules have a net orientation that is normal to the plane of the material.

13. An electro-optic device comprising a substrate, formed on the substrate, an elongate electrooptic waveguide having a channel formed of a heat-stable polymer matrix and dissolved therein, guest dipole molecules having one of the general forms shown in claim 10, the guest molecules having net dipole moments, said waveguide channel having selected switching regions in which the net dipole moments of the guest molecules are oriented directionally such that the index of refraction of said regions can be modulated for optical switching purposes by applying an electric field across said regions, in a field direction normal to the plane of the waveguide, and electrodes positioned on the waveguides, adjacent said selected regions, for use in selectively modulating the index of refraction of the regions by application of an electric field across the two electrodes.

14. The device of claim 13, wherein said waveguide channel contains dipolar molecules which are oriented directionally, and non-channel regions which are randomly oriented.

15. The device of claim 13, wherein said waveguide channel contains dipolar molecules which are oriented directionally, and non-channel regions in which the dipolar molecules are photobleached.

16. The waveguide material of claim 10, wherein said guest dipole molecules have the form shown at (A1).

17. The waveguide material of claim 10, wherein said guest dipole molecules have the form shown at (A2).

18. The waveguide material of claim 10, wherein said guest dipole molecules have the form shown at (A3).

19. The waveguide material of claim 10, wherein said guest dipole molecules have the form shown at (B).

20. The waveguide material of claim 19, wherein X is O.

21. The waveguide material of claim 20, wherein $R_1$–$R_4$ are methyl, and $R_5$ is selected from the group consisting of methyl, ethyl, propyl, 2-hydroxyethyl, and 3-hydroxypropyl.

22. The waveguide material of claim 21, wherein $R_5$ is selected from the group consisting of methyl, ethyl, and propyl.

23. The device of claim 13, wherein said guest dipole molecules have the form shown at (A1).

24. The waveguide material of claim 13, wherein said guest dipole molecules have the form shown at (A2).

25. The waveguide material of claim 13, wherein said guest dipole molecules have the form shown at (A3).

26. The waveguide material of claim 13, wherein said guest dipole molecules have the form shown at (B).

27. The waveguide material of claim 26, wherein X is O.

28. The waveguide material of claim 27, wherein $R_1$–$R_4$ are methyl, and $R_5$ is selected from the group consisting of methyl, ethyl, propyl, 2-hydroxyethyl, and 3-hydroxypropyl.

29. The waveguide material of claim 28, wherein $R_5$ is selected from the group consisting of methyl, ethyl, and propyl.

* * * * *